US010946051B2

(12) United States Patent
Martorell Guerola et al.

(10) Patent No.: US 10,946,051 B2
(45) Date of Patent: Mar. 16, 2021

(54) STRAIN OF *BIFIDOBACTERIUM ANIMALIS* SUBSP. LACTIS CECT 8145 AND USE THEREOF FOR THE TREATMENT AND/OR PREVENTION OF EXCESS WEIGHT AND OBESITY AND ASSOCIATED DISEASES

(71) Applicant: BIOPOLIS, S.L., Paterna (ES)

(72) Inventors: Patricia Martorell Guerola, Picasent (ES); Mª Empar Chenoll Cuadros, Pobla Vallbona (ES); Daniel Ramón Vidal, La Eliana (ES); Pepa Ortiz Serrano, Valencia (ES); Silvia Llopis Pla, Guadassequies (ES); Núria Gonzalez Martínez, Cheste (ES); Salvador Genovés Martínez, Aldaia (ES); Beatriz Casinos Ramo, Chiva (ES); Ángela Silva Angulo, Burjasot (ES); Amaya Aleixandre, Madrid (ES)

(73) Assignee: BIOPOLIS, S.L., Paterna (ES)

( * ) Notice: Subject to any disclaimer, the term of this patent is extended or adjusted under 35 U.S.C. 154(b) by 91 days.

(21) Appl. No.: 14/905,270

(22) PCT Filed: Jul. 17, 2014

(86) PCT No.: PCT/ES2014/070579
§ 371 (c)(1),
(2) Date: Jan. 14, 2016

(87) PCT Pub. No.: WO2015/007941
PCT Pub. Date: Jan. 22, 2015

(65) Prior Publication Data
US 2016/0143963 A1 May 26, 2016

(30) Foreign Application Priority Data

Jul. 18, 2013 (ES) ................ ES201331088

(51) Int. Cl.
| A61K 35/745 | (2015.01) |
| C12R 1/01 | (2006.01) |
| A23C 9/123 | (2006.01) |
| A23L 2/02 | (2006.01) |
| A23L 2/52 | (2006.01) |
| A23C 11/10 | (2006.01) |
| A23L 2/38 | (2006.01) |
| A23L 33/135 | (2016.01) |

(52) U.S. Cl.
CPC .......... *A61K 35/745* (2013.01); *A23C 9/1234* (2013.01); *A23C 11/106* (2013.01); *A23L 2/02* (2013.01); *A23L 2/382* (2013.01); *A23L 2/52* (2013.01); *A23L 33/135* (2016.08); *C12R 1/01* (2013.01); *A23Y 2300/21* (2013.01)

(58) Field of Classification Search
None
See application file for complete search history.

(56) References Cited

U.S. PATENT DOCUMENTS

| 2008/0267933 A1 | 10/2008 | Ohlson et al. |
| 2011/0027348 A1 | 2/2011 | Feher |
| 2012/0107291 A1 | 5/2012 | Burcelin et al. |

FOREIGN PATENT DOCUMENTS

| JP | 2011-172506 | * 9/2011 | ............... C12N 1/10 |
| WO | WO-2011083353 | 7/2011 | |

OTHER PUBLICATIONS

JP 2011-172506 English Translation.*
Rochet et al., Survival of Bifidobacterium animalis DN-173 010 in the faecal microbiota after administration in lyophilised form or in fermented product—a randomised study in healthy adults., J Mol Microbiol Biotechnol. 2008;14(1-3):128-36.*
Marteau et al., Bifidobacterium animalis strain DN-173 010 shortens the colonic transit time in healthy women: a double-blind, randomized, controlled study, Aliment Pharmacol Ther 2002; 16: 587±593.*
Guyonnet et al., Fermented milk containing Bifidobacterium lactis DN-173 010 improves gastrointestinal well-being and digestive symptoms in women reporting minor digestive symptoms: a randomised, double-blind, parallel, controlled study, British Journal of Nutrition (2009), 102, 1654-1662.*
Briczinski, Characterization of Strains of *Bifidobacterium animalis* subsp. *lactis* from commercial starter cultures, PhD Thesis, 2007 (Year: 2007).*
Palframan et al., Carbohydrate preferences of *Bifidobacterium* species isolated from the human gut, Curr. Issues Intest. Microbiol. (2003) 4:71-75 (Year: 2003).*
Madiedo et al., A Bile Salt-Resistant Derivative of Bifidobacterium animalis Has an Altered Fermentation Pattern When Grown on Glucose and Maltose, Applied and Environmental Microbiology, Nov. 2005, p. 6564-6570 (Year: 2005).*
Szajewska et al., The Effect of *Bifidobacterium animalis* ssp. *lactis* Supplementation in Preterm Infants: a Systematic Review of Randomized Controlled Trials, J Pediatr Gastroenterol Nutr. Aug. 2010 ; 51(2): 203-209 (Year: 2010).*

(Continued)

*Primary Examiner* — Louise W Humphrey
*Assistant Examiner* — Srikanth Patury
(74) *Attorney, Agent, or Firm* — Womble Bond Dickinson (US) LLP

(57) ABSTRACT

The invention is applicable within the food and pharmaceutical industry. More specifically, it relates to a novel strain of the species *Bifidobacterium animalis* subsp. *lactis* CECT 8145, the cell components, metabolites and secreted molecules thereof, which, incorporated into food and/or pharmaceutical formulations, can be used in the treatment and/or prevention of excess weight and obesity and related diseases such as metabolic syndrome, hypertension, glycemia, inflammation, type 2 diabetes, cardiovascular diseases, hypercholesterolemia, hormonal alterations, infertility, etc.

8 Claims, 11 Drawing Sheets

(56) References Cited

OTHER PUBLICATIONS

PCT Search Report and Written Opinion dated Nov. 18, 2014, PCT Appln. No. PCT/ES2014/070579, 9 pages.
Chenoll, E., et al., "Draft Genome Sequence of *Bifidobacterium animalis* subsp. *lactic* Strain CECT 8145, Able to Improve Metabolic Syndrome In Vivo", *Genome Announcements*, vol. 2, Issue 2, (Mar./Apr. 2014), 2 pages.
Molnar et al.. "Reduced antioxidant status in obese children with multimetabolic syndrome" International Journal of Obesity, vol. 28, Aug. 17, 2004, pp. 1197-2022.
Holscher et al. "*Bifidobacterium lactis* Bb12 Enhances Intestinal Antibody Response in Formula-Fed Infants: A Randomized, Doube-Blind, Controlled Trial", Journal of Parenteral and Enteral Nutrition, vol. 36, Supplement 1, Jan. 11, 2012.
Martorell et al., "Use of *Saccharomyces cerevisiae* and *Caenorhabditis elegans* as Model Organisms to Study the Effect of Cocoa Polyphenols in the Resistance to Oxidative Stress", Journal of Agricultural and Food Chemistry, vol. 59, No. 5, Mar. 9, 2011, pp. 2077-2085.

\* cited by examiner

STRAIN OF *BIFIDOBACTERIUM ANIMALIS* SUBSP. LACTIS CECT 8145 AND USE THEREOF FOR THE TREATMENT AND/OR PREVENTION OF EXCESS WEIGHT AND OBESITY AND ASSOCIATED DISEASES

CROSS-REFERENCE TO RELATED APPLICATIONS

The present patent application is a national phase application of International Application No. PCT/ES2014/070579, filed Jul. 17, 2014, which claims priority to Spanish Application No. P201331088, filed Jul. 18, 2013, the disclosures of which are incorporated herein by reference.

TECHNICAL FIELD OF THE INVENTION

The present invention falls within the food and pharmaceutical industry. It relates in particular to a new strain of the species *Bifidobacterium animalis* subsp. *lactis* CECT 8145, its supernatants and/+ or culture, as well as extracts and/or bioactive compounds released by the strain that, added to food and/or pharmaceutical formulations, induce satiety, reduce appetite and reduce body fat, decrease cardiovascular risk, cause weight loss, have antioxidant and anti-inflammatory activity and, therefore, have application in the treatment and/or prevention of overweight and/or obesity and/or associated diseases/disorders.

BACKGROUND OF THE INVENTION

Obesity and overweight are metabolic and nutritional disorders with serious health consequences, overweight being a degree of obesity. Despite improved clinical and epidemiological knowledge of this problem, the prevalence of obesity and overweight has increased significantly in industrialized and developing countries. Obesity is a recognized high-risk factor in the incidence of various chronic diseases/disorders such as hypertension, ischemic heart disease, brain stroke, type-2 diabetes and certain forms of cancer, which are important causes of morbidity and mortality in developing countries in the Western world.

In the struggle against overweight and obesity, the food industry has introduced new ingredients in order to help consumers maintain an appropriate weight. In the field of research and new product development, one option is to add certain ingredients that act by inhibiting the accumulation of energy as fat, either by decreasing fat absorption or formation, or by stimulating fat mobilization with increased lipolysis, or by improving lipid oxidation rates.

Another strategy that acts positively on the prevention or treatment of overweight and obesity is to control and/or reduce appetite by the induction of satiety, activating the metabolic regulation of appetite.

Similarly, some studies suggest that obesity is accompanied by a state of chronic oxidative stress, which has been proposed as the link between obesity and some comorbidities such as insulin resistance and cardiovascular disease. (Molnar D, Decsi T, Koletzko B. "Reduced antioxidant status in obese Children with multimetabolic syndrome" *Int J. Obes Relat Metab Disord* 2004; 28:1197-202). Consequently, in recent years there has been research into the possible use of dietary supplements with antioxidants to improve and prevent overweight and obesity.

Moreover, the intestinal microbiota and probiotics have a positive effect on health by regulating immunological functions and protecting the individual from infections and chronic inflammatory conditions. Studies indicate that the intestinal microbiota is a factor that may play a role in regulating body weight and obesity-associated diseases/disorders. Therefore, manipulation of the intestinal microbiota through diet is proposed as a potential new tool to prevent or alter the risk of obesity, and particularly the associated metabolic diseases/disorders.

In this respect, numerous beneficial effects have been attributed to strains belonging to species *Bifidobacterium animalis* subsp. *lactis* in relation to the treatment or prevention of overweight and obesity and associated diseases/disorders. The U.S. patent document US2011027348 describes the microorganism *Bifidobacterium animalis* subsp. *lactis* (specific strain unspecified), with activity against inflammation, metabolic syndrome, obesity and hypertension.

In addition, other specific examples in this respect are the strains *Bifidobacterium animalis* subsp. *lactis* B420 and Bb12.

Thus, in the paper entitled "*Study of Danisco probiotics shows positive impact on metabolic syndrome (MetS)*", *Food Engineering & Ingredients*, 2010, Vol. 35, Issue 2, p. 9, DuPont, describes the strain *Bifidobacterium animalis* subsp. *lactis* B420 and its activity against metabolic syndrome, inflammation, metabolic endotoxemia, etc.

Similarly, the U.S. patent document US20120107291 describes the strain *Bifidobacterium animalis* subsp. *lactis* B420 with activity against diabetes, metabolic syndrome, obesity, tissue inflammation, etc.

According to information in the said patent application, strain B420 acts by positively influencing the immune system via the gut-associated lymphoid tissue and displays the ability to improve glucose tolerance, reduce mesenteric fatty tissue, reduce inflammatory indices, etc. However, the information available on this strain does not mention anything regarding its possible ability to induce a reduction in appetite or increase satiety nor does it claim the antioxidant capacity of the said strain.

The non-patent reference document, entitled "*Bifidobacterium lactis Bb12 enhances intestinal antibody response in formula-fed infants: a randomized, double-blind, controlled trial*", by Holscher et al., describes the strain *Bifidobacterium lactis* Bb12 and its role in boosting immune function.

The U.S. patent document US2008267933 describes the strain *Bifidobacterium animalis* subsp. *lactis* Bb12 which exerts anti-obesity and weight control activity by inducing satiety, improving energy metabolism, improving insulin sensitivity and metabolic syndrome, etc. The effects of this strain may be a result of overexpression of certain genes, such as Scd1, Acrp30, Adn, Thrsp, Car3 and Apoa-4, related to energy, fat, insulin and glucose metabolism, in addition to the satiety. However, in the information available on the said strain there is no mention whatsoever of its possible antioxidant capacity.

In consideration of the above, the technical problem object of the present invention relates to the provision of novel microorganisms that can be used as ingredients in food and pharmaceutical formulations to provide improved therapeutic and/or preventive activity against overweight and obesity and associated diseases/disorders.

The above described technical problem has been solved by the provision of strain *Bifidobacterium animalis* subsp. *lactis* deposited on the 14 May 12 under accession number: CECT8145 in the Colección Española de Cultivos Tipo (Spanish Type Culture Collection—CECT), located at Parc Cientific Universitat de Valencia, c/ Catedrático Agustin Escardino, 9, 46980 Paterna—Valencia, Spain, under the provisions of the Budapest Treaty, as well as food and pharmaceutical formulations containing the said strain.

Unlike strains belonging to the same species in the prior art, in addition to reducing body fat, ingestion of the strain of the present invention, and food and pharmaceutical formulations containing the said strain, can induce satiation and reduce appetite as well as increase resistance to oxidative stress in mammals. Additionally, the strain of the present invention, as well as the dietary and pharmaceutical formulations containing it, reduce total cholesterol and triglyceride levels in blood, in addition to reducing the concentration of glucose and some inflammatory markers. All this leads to the conclusion that the effects of the strain of the present invention, as well as the food and pharmaceutical formulations containing the said strain, are effective in the management of overweight, that is, in the treatment and/or prevention of obesity and associated diseases/disorders and that the strain of the present invention is superior to other strains of the same species in the prior art.

BRIEF DESCRIPTION OF THE INVENTION

The present invention relates to a new strain of the species *Bifidobacterium animalis* subsp. *lactis*, deposited on the 14 May 12 under accession number CECT8145 in the Colección Española de Cultivos Tipo (Spanish Culture Type Collection—CECT), located at Parc Cientific Universitat de Valencia, c/ Catedrático Agustin Escardino, 9, 46980 Paterna—Valencia, Spain, under the provisions of the Budapest Treaty, as well as the bioactive compounds released by this strain, the supernatants and the cultures of the strain, the extracts containing the biaoactive compounds, supernatants and/or cultures, and the formulation of any of these in food and pharmaceutical formulations.

The strain of the invention and products derived thereof, object of the present invention, act by modulating the differential expression of certain genes that positively affect the reduction of body fat, which makes the strain of the present invention particularly effective in the treatment and/or prevention of overweight and/or obesity and associated diseases/disorders, such as: metabolic syndrome, hypertension, hyperglycemia, inflammation, type-2 diabetes, cardiovascular disease, high cholesterol, hormonal disorders, infertility, etc.

After mammals ingested the strain of the present invention, they experienced a reduction in body fat and weight, in total triglyceride, total cholesterol, glucose levels and TNFα factor, and an increase in adiponectin. Additionally, it led to an increase in satiety as demonstrated by a reduction in ghrelin levels, as well as an increase in resistance to oxidative stress, as demonstrated by a reduction in the concentration of malondialdehyde in mammals treated with the strain of the present invention.

The transcriptomic study of the strain of the present invention shows that intake of the said strain up-regulates metabolic pathways and processes related to the metabolism of carbohydrates (including oxidative phosphorylation and ATP synthesis), glutathione metabolism (reduction in oxidative stress levels), the biosynthesis of cofactors and vitamins, lipid metabolism, nucleotide metabolism, glycosylation and membrane metabolism.

Moreover, as confirmed by the metabolomic study of the strain of the present invention, details of which are provided in the experimental part of the patent specification, the intake of this strain induces a series of metabolic changes associated with the antioxidant metabolism and with the metabolism of carbohydrates and nucleotides. Regarding the reduction in oxidative stress levels, the glutathione metabolism is identified as a target of the present strain, and an up-regulation of the pentose phosphate pathway and of glycosylation are notable, also various changes in the metabolism of glycogen, nucleotides, lipids and cofactors are apparent.

DETAILED DESCRIPTION OF THE INVENTION

The object of the present invention is a microorganism, as well as the food and pharmaceutical formulations containing it, which has useful application to the treatment and prevention of overweight and obesity in mammals and related diseases/disorders. The said microorganism relates, specifically, to a new strain of the species *Bifidobacterium animalis* subsp. *lactis*, deposited on the 14 May 12 under accession number: CECT8145 in the Colección Española de Cultivos Tipo (Spanish Culture Type Collection—CECT), located at Parc Cientific Universitat de Valencia, c/ Catedrático Agustin Escardino, 9, 46980 Paterna—Valencia, Spain, under the provisions of the Budapest Treaty.

In this patent application, the strain of the invention *Bifidobacterium animalis* subsp. *lactis* CECT8145 is also referred to as BIF-1.

For the purposes of the present invention, the terms "related or associated diseases/disorders" and "diseases/disorders caused by overweight and/or obesity" comprise: metabolic syndrome, hypertension, hyperglycemia, inflammation, type-2 diabetes, cardiovascular disease, hypercholesterolemia, hormonal disorders, infertility, etc.

For the purposes of the present invention, the term bioactive products derived from the strain of the present invention, are defined as its cell components, and the compounds and molecules that form part of the strain, such as the metabolites and molecules secreted thereof, such as: intracellular components (e.g., DNA, peptides, fatty acids, etc.) cell-wall components (proteins, peptides, fatty acids, etc.) that confer the desired preventive or therapeutic activity.

The term food formulation is defined as functional foods, probiotics, synbiotics, dietary supplements and/or nutraceutical incorporating strain of the present invention, the bioactive products derived thereof, the supernatant and/or extract and/or the culture of the same.

In the context of the present invention, pharmaceutical formulations are defined as those which incorporate the strain of the present invention, the bioactive products derived thereof, the supernatant and/or extract and/or culture of the same, combined with, at least one pharmaceutically acceptable excipient and/or carrier. Pharmaceutically acceptable excipients and/or carriers used in the present invention are known in the prior art to experts in the art.

The inventors of the present invention have identified a new strain, namely CECT8145 belonging to the species *Bifidobacterium animalis* subsp. *lactis*, which has novel biological activities compared with other strains of the same species reported in the prior art, making it particularly effective in the treatment and/or prevention of overweight and/or obesity and the diseases/disorders caused by and/or related to overweight and/or obesity.

Comparative genomic studies between the strain of the present invention and other strains belonging to the same species of the prior art, namely, strains B420 and Bb12, show that the strain of the present invention has genes and genome regions that are unique and do not have corresponding homologues in the other two strains (B420 and Bb12). Specifically, the genomic studies conducted determined that the strain of the present invention, unlike strains B420 and Bb12, lack genes corresponding to molecular lipid-binding function.

One of the novel biological activities of the strain of the present invention is its antioxidant activity and, consequently, its ability to increase resistance to oxidative stress.

Oxidative stress is caused by an imbalance between free-radical production and the antioxidant defences that are responsible for detoxifying the said radicals in the organism. In obese patients, oxidative stress is not generated by a single mechanism but by the confluence of several factors that may, ultimately, be summarized as a decrease in antioxidants together with an increase in pro-oxidant elements. Several studies report a direct relationship between obesity and decreased activity of the main antioxidant enzymes.

The resistance to oxidative stress induced by the biological activity of the strain of the present invention is demonstrated by the reduction in malondialdehyde concentrations in mammals treated with the strain of the present invention (FIG. 16).

Malondialdehyde is a marker indicating oxidation rates in the body: the level of this marker increases parallel to the increase in oxidation rates, with reduced protection against oxidative stress; and vice versa.

FIG. 5 shows that ingestion of the strain of the present invention increases protection against oxidative stress, as demonstrated by the survival of *Caenorhabditis elegans*.

Another novel biological activity of the strain of the present invention is its ability, after ingestion, to increase satiety, reducing ghrelin levels (FIG. 17).

Ghrelin is the only known circulating hormone that can potentially increase or stimulate appetite and therefore acts as a regulator of hunger and body weight. It is a gastrointestinal neuropeptide (endogenous ligand of the growth hormone secretagogue receptor) recently isolated from the oxyntic mucosa produced mainly in the stomach. Its concentration in blood depends on diet, hyperglycemia, adiposity and leptin. It is secreted 1-2 hours before eating and its concentration decreases dramatically after eating. It acts in the lateral hypothalamus and, theoretically, inhibits proinflammatory cytokine secretion and antagonizes leptin. Ghrelin physiologically increases gastric acid secretion and has other hormonal and cardiovascular functions.

The strain of the present invention is capable of decreasing ghrelin levels, thus increasing satiety.

Additionally, the strain of the present invention causes a reduction in the level of total triglycerides, cholesterol, glucose, TNFα factor, and an increase in adiponectin levels (FIGS. 12, 9, 13, 14 and 15, respectively).

It has been shown that the reduction in body fat levels resulting from ingestion of the strain of the present invention are surprisingly higher than the levels corresponding to other strains of the genus *Bifidobacterium* and, in particular, compared to the commercial strain *Bifidobacterium animalis* subsp. *lactis* Bb12, belonging to the same species (FIG. 2).

The results illustrated in Example 1 herein confirm that the ingestion of the strain of the present invention reduces body fat in the nematode *Caenorhabditis elegans* by at least 40%, compared to control feeding conditions. Compared to body-fat reduction produced by other strains of the same species of prior art and, in particular, compared to strain Bb12, the strain of the present invention is able to cause body-fat reduction levels 28.5% higher than strain Bb12; which demonstrates that strain BIF-1 of the present invention is more effective than other strains of the same species.

Likewise, when the strain of the present invention is incorporated into a food product, such as yogurt, fermented soy or juice, its effect on body-fat reduction is over 11% higher than the effect produced by conventional products: yogurt, fermented soy or juice (FIGS. 20, 21 and 22).

As reported in detail in the experimental part provided as way of example, the transcriptomic study shows that ingestion of the strain of the present invention up-regulates the metabolic pathways and processes related to carbohydrate metabolism (including, oxidative phosphorylation and ATP synthesis) glutathione metabolism (reduced oxidative stress levels), the biosynthesis of cofactors and vitamins, lipid metabolism, nucleotide metabolism, glycosylation and membrane metabolism.

Moreover, as confirmed from the metabolomic study, details of which are provided in the experimental part of the patent specification, the ingestion of this strain induces a series of metabolic changes associated with antioxidant metabolism and carbohydrate and nucleotide metabolism. Glutathione metabolism is identified as a target of this strain for the reduction of oxidative stress levels, and the up-regulation of the pentose phosphate pathway and of glycosylation is also notable, with various changes also being apparent in glycogen, nucleotide, lipid and cofactor metabolism. Said metabolonomic changes confirm the biological activities related to body-fat reduction, and protection against oxidative stress induced by the strain of the present invention.

These results have been confirmed by a study with mutants of the nematode *C. elegans* as explained in detail in Example 8, which identified several genes that are differentially expressed after ingestion of strain BIF-1 of the present invention, and explain the biological activities exerted by this strain and its more effective action against overweight and obesity.

Specifically, we have identified the following differentially expressed genes: Acox-1, Acs-5, Daf-22, Fat-7, Daf-16, Sod-4, Trxr-2, Asg-2 and Tph-1.

Genes Acox-1, Acs-5 and Daf-22 encode enzymes of fatty acid beta-oxidation in peroxisome; genes Fat-7 and Daf-16 encode the enzymes involved in the fatty-acid desaturation process; genes Sod-4, Trxr-2 and Asg-2 encode enzymes involved in maintaining the redox cell balance and removing ROS; gene Asg-2, alone, encodes an enzyme involved in oxidative phosphorylation processes; and gene Tph-1 encodes an enzyme involved in triprophan metabolism and hence in serotonin synthesis.

The strain of the present invention and the bioactive products secreted thereof, as well as the supernatants, the culture and/or extracts of the said strain, can be formulated, individually or in combination with other microorganisms and/or functional ingredients, and incorporated into food or pharmaceutical formulations for use in accordance with the present invention.

When the strain of the present invention is incorporated into food or pharmaceutical formulations in combination with other microorganisms, the latter should preferably belong to the genera *Lactobacillus, Streptococcus, Bifidobacterium, Saccharomyces* and/or *Kluyveromyces*, such as for example: *L. rhamnosus, L. delbrueckii* subsp. *bulgaricus, L. kefir, L. parakefir, L. brevis, L. casei, L. plantarum, L. fermentum, L. paracasei, L. acidophilus, L. paraplantarum, L. reuteri, St. thermophilus, B. longum, B. breve, B. bifidum, B. catenulatum, B. adolescentis, B. pseudocatenulatum, S. cerevisiae, S. boulardii, K. lactis,* or *K. marxianus*.

The present invention also relates to a formulation incorporating the bioactive compounds derived from the strain of the present invention, the supernatants and/or cultures of the strain, as well as the extracts obtained from culturing the strain of the invention.

Formulations with the present invention, incorporating the strain of the present invention and/or bioactive products secreted thereof and/or supernatants and/or cultures and/or extracts may be food or pharmaceutical formulations.

The said food or pharmaceutical formulations may be in liquid or solid, including but not limited to, capsules and/or pills.

The food and/or pharmaceutical formulations of the present invention incorporate the strain of the present invention in an amount between $10^5$ CFU and $10^{12}$ CFU per gram or millilitre of formulation, and preferably between $10^7$ and $10^{11}$ CFU/g or CFU/ml.

When the food and/or pharmaceutical formulations of the present invention incorporate the bioactive compounds derived from the strain of the present invention, such as supernatants, extracts, peptides, etc., these are incorporated into the formulation in a proportion of between 0.01 and 99% by weight of the total formulation and preferably in a proportion of between 0.01 and 40%. The nutritional formulations incorporating the strain of the present invention, as well as the bioactive compounds derived thereof, supernatants, culture extracts and/or culture, should preferably be one of the following: fruit or vegetable juice, ice cream, infant formula, milk, yogurt, cheese, fermented milk, powdered milk, cereals, bakery products, milk- and/or cereal-based products, nutritional supplements, soft drinks and/or dietary supplements.

The dairy food products to which this invention makes reference, such as fermented milk, fresh cheese or yogurt, or their equivalents, dried or freeze-dried, are the preferred suitable vehicles in which to incorporate the strain of the present invention and/or the bioactive compounds derived thereof and/or the supernatants and/or extracts and/or culture.

The strain of the present invention and/or the derived bioactive compounds thereof and/or the supernatants and/or extracts and/or culture of the strain may, if necessary, be packaged in gelatine or cellulose capsules or, gel capsules or pills, among other formats, as food or pharmaceuticals.

The strain of the invention and formulations containing it, are specially designed for use in mammals, i.e., animals and humans, for the treatment of overweight and obesity and related diseases/disorders.

They are therefore objects of the present invention, strain *Bifidobacterium animalis* subsp. *lactis* CECT8145, food and pharmaceutical formulations that comprise the said strain, in culturable and/or nonculturable and/or nonviable form and optionally in combination with other microorganisms, as well as a method to treat and/or prevent overweight and/or obesity in mammals and associated diseases/disorders, such as: metabolic syndrome, hypertension, hyperglycemia, inflammation, type-2 diabetes, cardiovascular disease, hypercholesterolemia, hormonal disorders and infertility, characterized by comprising the administration of an effective amount of the strain of the invention, *Bifidobacterium animalis* subsp. *lactis* CECT8145, as well as food and pharmaceutical formulations that contain it in accordance with the present invention.

Within the context of the present invention, also an object of the invention is a method to reduce weight, total cholesterol, triglycerides and glucose levels in blood, levels of TNFα factor, malondialdehyde and ghrelin, as well as to increase adiponectin in mammals, characterized by comprising the administration of an effective amount of the strain of the invention, *Bifidobacterium animalis* subsp. *lactis* CECT8145, as well as the food and pharmaceutical formulations containing it in accordance with the present invention.

In this respect, it is noteworthy that the present invention contemplates the use of strain of the invention, *Bifidobacterium animalis* subsp. *lactis* CECT 8145, both in its culturable and/or nonculturable and/or nonviable cell forms (FIG. 4).

Nonculturable and/or nonviable cells of the invention, inactivated by different methods (freezing, heat, radiation, etc.) can be used according to the present invention, and form part of the present invention, since the desired effects are exerted, at least partially, by structural components (such as DNA, cell wall components, etc.). This means the strain of the present invention retains some of its properties against metabolic syndrome and related diseases/disorders without necessarily being culturable/viable. Thus, as shown in Example 4, an inactivated culture of the strain of the present invention reduces body fat in the animal model *C. elegans*, which suggests that the functional effect is not due only to the metabolism of the strain, but to the presence of certain cell-wall compounds.

The following figures and examples are provided below in order to illustrate the present invention and are in no way intended to be limiting of the present invention.

EXAMPLES

Example 1

Screening Bacteria for Body-Fat Reduction in *Caenorhabditis elegans*.

Twenty-three strains of the genus *Lactobacillus* and 15 strains of the genus *Bifidobacterium* was screened to analyze their effect on body-fat reduction after being ingested by the nematode *Caenorhabditis elegans*. Two commercial strains were included in the study, LGG (*Lactobacillus rhamnosus*) and Bb12 (*B. animalis* subsp. *lactis*).

*Caenorhabditis elegans* accumulates fat in the form of droplets that can be visualized by staining with Nile red (fluorescent). The fluorescence emitted from said dye can be quantified by fluorimetry. Therefore, various microorganisms were assessed for their effect on body-fat accumulation and/or reduction in the nematode by analyzing the reduction in fluorescence in worms fed with different strains, compared to worms fed under control conditions (NG medium+*Escherichia coli*).

The experiments consisted of feeding *C. elegans* with different microorganisms, for the period lasting from the egg to the young adult stage (3 days old). The standard feed was NG medium sown with the bacterium *Escherichia coli*.

Fat droplets were stained by direct addition of Nile red dye to the plates of NG medium. Nematodes were incubated at 20° C. under the different feeding conditions throughout the test period. After the feeding period, samples of each condition were taken and the fluorescence emitted in each case was quantified. The control feeding condition (NG medium+*Escherichia coli*) was taken as reference to quantify and compare fluorescence under the experimental conditions.

Figure 1:
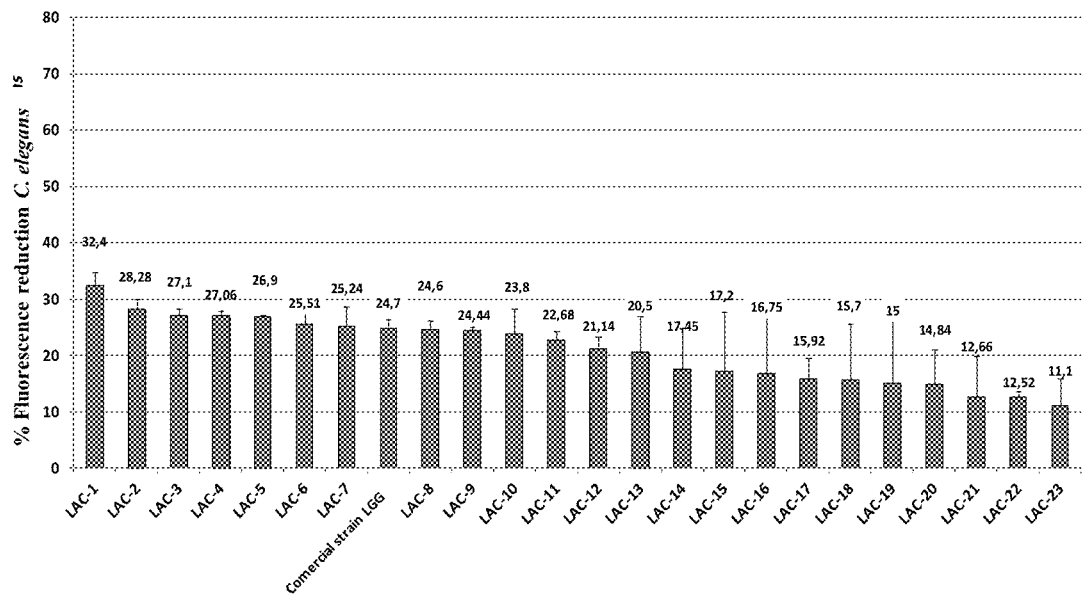
FIG. 1: Screening of 23 strains of the genus *Lactobacillus* for body-fat reduction in *C. elegans*.

FIG. 1 shows the results obtained with *Lactobacillus* strains for body-fat reduction in *C. elegans* (expressed as a percentage of fluorescence reduction quantified in worms stained with Nile red dye.) The highest fat-reduction percentage corresponded to the LAC-1 strain (32.4% compared to control feeding conditions).

Figure 2:
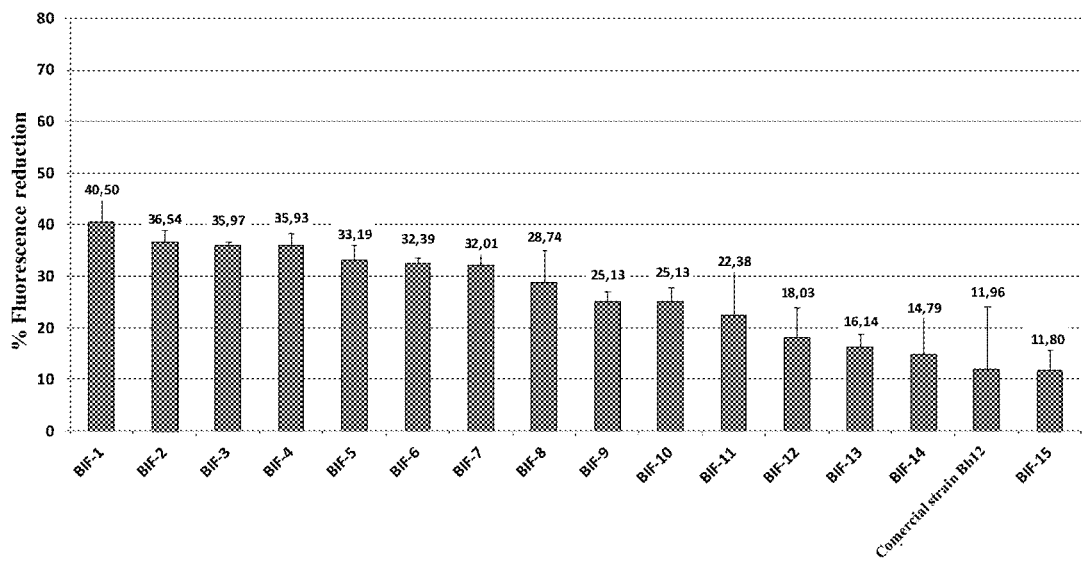
FIG. 2: Screening of 15 strains of the genus *Bifidobacterium* for body-fat reduction in *C. elegans*.

FIG. 2 shows the screening of *Bifidobacterium* strains. The most effective strain for body-fat reduction was BIF-1 (40.5% compared to control feeding conditions).

Based on the results obtained from the 38 strains tested, the strain *Bifidobacterium* BIF-1 was selected as the most effective against fat reduction. Accordingly we studied the functional and technological properties of this strain in greater depth.

Example 2

Taxonomic Identification and Genomic Sequencing 2.1. Identification

Strain BIF-1 was identified unambiguously at genus and species level by sequencing the ribosomal DNA (rDNA) 16S. The sequence was identified by comparing the BIF-1 strain sequence with the complete gene sequences deposited in public databases using the BLAST online (http://blast.ncbi.nlm.nih.gov/Blast.cgi), the highest homology (99%) was obtained with public sequences belonging to the species *B. animalis* subsp. *lactis*.

2.2. Genome Sequencing

In order to characterize the genomic level and safety and functionality of strain BIF-1 we performed whole-genome sequencing of strain BIF-1 by pyrosequencing on a Life Science-Roche 454 platform. A total of 434,581 raw sequences were obtained. Further de novo sequence assembly organized sequences on five scaffolds, the largest being 1,923,368 nucleotides. The genome size of strain BIF-1 is estimated at 2.1 Mb. Genes encoding virulence factors were not detected nor were antibiotic resistance genes located in areas at risk of horizontal transfer.

Example 3

Quantification of Triglyceride Reduction in BIF-1-Treated *C. Elegans*

The effect of strain BIF-1 ingestion on triglyceride reduction was analyzed in *C. elegans* wild-type N2.

Triglycerides were determined from synchronized young adult *C. elegans* populations. Nematodes from each condition were washed in PBS buffer and sonicated for lysate. Lysed samples were used to determine total triglycerides using a commercial kit based on fluorimetric determination. All samples were normalized for protein concentration.

Figure 3:
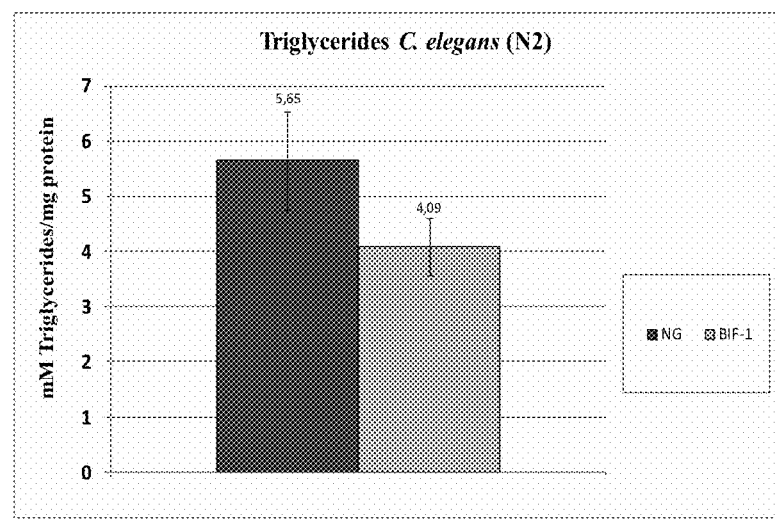
FIG. 3: Quantification of triglycerides in *C. elegans* wild-type N2 fed on strain CECT8145 (BIF-1) or given a control diet (nematode growth medium, hereafter NG medium).

FIG. 3 shows triglyceride quantification for nematodes under control feeding conditions (NG medium) or fed on strain BIF-1. A reduction was observed in total triglycerides in the BIF-1-fed nematodes.

Example 4

Body-Fat Reduction in *C. elegans* Treated with an Inactivated Culture of BIF-1

The fat-reducing functional effect of inactivated BIF-1 cells was analyzed in *C. elegans*. Cells were inactivated by heat treatment at 70° C. for 18 hours.

The tests consisted in feeding *C. elegans* with activated or inactivated BIF-1 from the egg to the adult stage (3 days). In control conditions, nematode were fed NG medium, containing *Escherichia coli*.

Fat droplets were stained by direct addition of Nile red dye to the plates of NG medium. Nematodes were incubated at 20° C. under the various conditions during the test period. After the feeding period, samples were taken of each condition and the fluorescence emitted in each case was quantified. The control feeding condition (NG medium+*Escherichia coli*) was taken as a reference to quantify fluorescence of the other experimental conditions.

Figure 4:
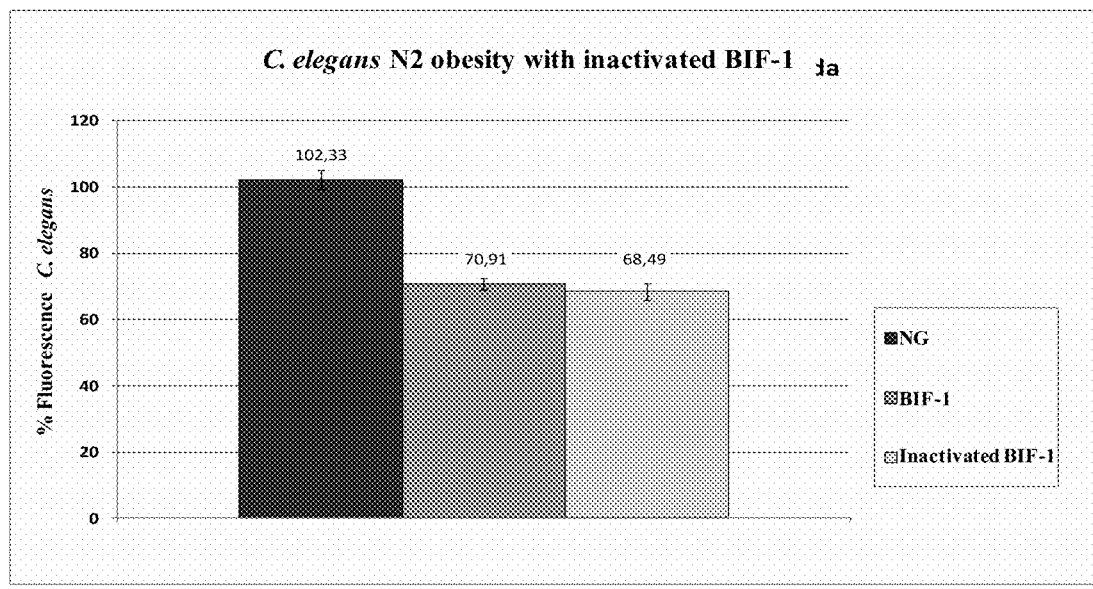
FIG. 4: Effect of a culture of strain CECT8145 (BIF-1) inactivated at 70° C. overnight on body-fat reduction in *C. elegans*.

The results (FIG. 4) show that cells of BIF-1 inactivated at 70° C. maintained their fat-reducing effect in the nematode, as the same percentage of fluorescence was observed as in live BIF-1 culture.

Example 5

Antioxidant Activity of Strain BIF-1 in *C. elegans*

We analyzed whether the ingestion of strain BIF-1 increased resistance to acute oxidative stress in *C. elegans* (wild-type N2).

Figure 5:
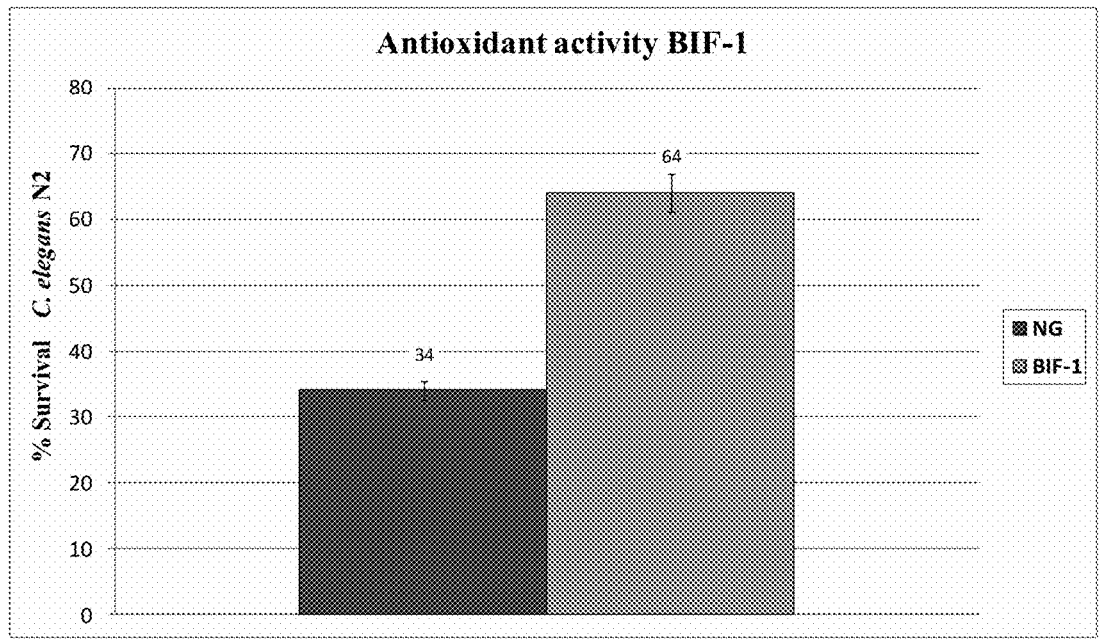
FIG. 5: Antioxidant activity of strain CECT8145 (BIF-1) estimated after subjecting *C. elegans* (wild type N2) to oxidative stress by applying hydrogen peroxide.

The tests were carried out following the Methodology described by Martorell et al. (2011). *C. elegans* wild-type N2 was used. Trials included a control (NG medium+*E. coli* strain OP50) and the BIF-1 strain. Trials were started with age-synchronized nematode populations, which were cultured in NG plates under the different feeding conditions. The plates were incubated at 20° C. for 7 days. After this period, oxidative stress was applied with $H_2O_2$ (2 mM), and nematode viability was determined after 5 hours of incubation. FIG. 5 shows the results obtained in nematode survival after applying hydrogen peroxide stress. Nematodes fed for 7 days with BIF-1 were much more resistant to oxidative stress, with increased survival as compared to the population under control-feeding conditions.

Example 6

Transcriptomic Study in *C. elegans* with the Strain *Bifidobacterium animalis* subsp. *lactis* BIF-1

We studied the effect of *B. animalis* subsp. *lactis* BIF-1 ingestion on the *C. elegans* transcriptome. Technology "chips" were used to study changes in gene expression, in metabolic pathways and biological processes in nematodes fed BIF-1 as compared to nematodes under control feeding conditions. The significance level $P \leq 0.05$ was used in the statistical analysis.

6.1. Differential Gene Expression in BIF-1-Treated Nematodes

Nematodes fed strain BIF-1 showed a different gene-expression profile compared to nematodes under control feeding conditions. Thus, they presented 296 over-expressed genes and 26 under-expressed genes compared to control nematodes (Table 1).

TABLE 1

Differential gene expression observed in *C. elegans* fed the BIF-1 strain.

| | Number genes under-expressed | Number genes without differential expression | Number over-expressed genes |
|---|---|---|---|
| BIF-1-treated vs Control | 26 | 22303 | 296 |

Screening of the 296 genes over-expressed in BIF-treated nematodes revealed different functional groups. The aforementioned genes are related to proteolysis, reproduction, embryonic development, carbohydrate metabolism, molting cycle, body morphogenesis, locomotion, redox processes, protein metabolism, transport, glutathione metabolism, aromatic amino acid metabolism, response to gamma radiation, fatty acid metabolism and neuropeptide signalling pathways.

The 26 under-expressed genes in BIF-1-treated *C. elegans* are mainly related to upregulation of growth.

6.2. Metabolic Pathways

Concerning the metabolic pathways, it was determined that Nematodes fed BIF-1 exhibited 23 upregulated and 20 downregulated metabolic pathways compared to control nematodes (Table 2).

Tables 3 and 4 list the upregulated or downregulated metabolic pathways after treatment with the BIF-1 bifidobacteria strain.

TABLE 2

Number of metabolic pathways differentially expressed in *C. elegans* fed strain BIF-1.

| | Number downregulated metabolic pathways | Number unaffected metabolic pathways | Number upregulated metabolic pathways |
|---|---|---|---|
| BIF-1-treated vs. control | 20 | 55 | 23 |

TABLE 3

List of upregulated metabolic pathways in *C. elegans* after BIF-1 treatment compared with the Control. ID: identification according to KEGG database.

| ID KEGG | Metabolic pathways upregulated in BIF-treated vs. Control |
|---|---|
| 00190 | Oxidative phosphorylation |
| 00480 | Glutathione metabolism |
| 00982 | Drug metabolism - cytochrome P450 |
| 00980 | Metabolism of xenobiotics by cytochrome P450 |
| 00983 | Drugs metabolism - other enzymes |
| 00670 | Folate biosynthesis (vitamins and cofactors metabolism) |
| 04142 | Lysosome |
| 00260 | Glycine, serine and threonine metabolism |
| 00330 | Arginine and proline metabolism |
| 00860 | Porphyrin and chlorophyll metabolism |
| 00270 | Cysteine and methionine metabolism |
| 01040 | Unsaturated fatty acid biosynthesis |
| 00040 | Pentose and glucuronate interconversions |
| 04146 | Peroxisome |
| 00590 | Arachidonic acid metabolism |
| 00053 | Ascorbate and aldarate metabolism |
| 00514 | Other types of O-glycan biosynthesis |
| 00910 | Nitrogen metabolism |
| 00250 | Metabolism of alanine, aspartate and glutamate |
| 00380 | Tryptophan metabolism |
| 00620 | Pyruvate metabolism |

TABLE 3-continued

List of upregulated metabolic pathways in *C. elegans* after BIF-1 treatment compared with the Control. ID: identification according to KEGG database.

| ID KEGG | Metabolic pathways upregulated in BIF-treated vs. Control |
|---|---|
| 00650 | Butanoate metabolism |
| 00410 | Beta-alanine metabolism |

TABLE 4

List of downregulated metabolic pathways in BIF-1-treated *C. elegans* compared to the Control. ID: identification according to KEGG database.

| ID KGGE | Metabolic pathways downregulated in BIF-treated vs. Control |
|---|---|
| 04330 | Notch signalling pathway |
| 03440 | Homologous recombination |
| 04340 | Hedgehog signalling pathway |
| 03410 | Damaged DNA repair (base excision repair) |
| 04310 | Wnt signalling pathway |
| 03018 | RNA degradation |
| 04710 | Circadian rhythm |
| 04150 | mTOR signalling pathway |
| 03430 | Damaged-DNA repair (mismatch repair) |
| 03420 | Nucleotide excision repair |
| 03050 | Proteasome |
| 03013 | RNA transport |
| 04350 | TGF-beta signalling pathway |
| 03015 | mRNA surveillance pathways |
| 03040 | Spliceosome |
| 04120 | Ubiquitin-mediated proteolysis |
| 03030 | DNA replication |
| 04141 | Protein processing in endoplasmic reticulum |
| 04144 | Endocytosis |
| 04914 | Progesterone-mediated oocyte maturation |

6.3. Biological Processes

In nematodes fed strain BIF-1, a total of 26 biological processes were over-expressed while 76 processes were under-expressed as compared to the Control (Table 5).

TABLE 5

Number of biological processes differentially expressed in *C. elegans* fed strain BIF-1 compared to the Control.

| | Under-expressed GO | Over-expressed GO |
|---|---|---|
| BIF-1-treated vs. Control | 76 | 26 |

Tables 6 and 7 list of the over-expressed and under-expressed processes in BIF-1-treated nematodes in detail.

TABLE 6

List of the 26 biological processes over-expressed in BIF-1-treated *C. elegans*. GO: Gene Ontology (database).

| GO | Name |
|---|---|
| GO: 0030259 | Lipid glycosylation |
| GO: 0006937 | Regulation of muscle contraction |
| GO: 0042775 | Mitochondrial ATP synthesis coupled to electron transport chain |
| GO: 0009156 | Ribonucleoside monophosphate biosynthetic processes |
| GO: 0034220 | Transmembrane ion transport |
| GO: 0009072 | Aromatic amino acid metabolism processes |
| GO: 0030241 | Skeletal muscle myosin thick filament assembly |
| GO: 0009112 | Nucleobases metabolism processes |
| GO: 0015992 | Proton transport |
| GO: 0006508 | Proteolysis |
| GO: 0040018 | Positive regulation of multicellular organism growth |
| GO: 0034607 | Behavior involved in mating |
| GO: 0007218 | Neuropeptide signalling pathway |
| GO: 0046942 | Carboxylic acid transport |
| GO: 0072529 | Catabolic processes of pyrimidine containing compounds |
| GO: 0042398 | Modified amino acid biosynthetic process |
| GO: 0015833 | Peptide transport |
| GO: 0006754 | ATP biosynthesis processes |
| GO: 0009063 | Cellular amino acid catabolic process |
| GO: 0048521 | Negative regulation of behaviour |
| GO: 0055074 | Calcium ion homeostasis |
| GO: 0006637 | Acyl-CoA metabolic processes |
| GO: 0042338 | Cuticle development involved in collagen and cuticulin-based cuticle molting cycle |
| GO: 0006814 | Sodium ion transport |
| GO: 0036293 | Response to decreased oxygen levels |
| GO: 0009069 | Serine family amino acid metabolic process |

TABLE 7

List of the 76 biological processes under-expressed in BIF-1-treated *C. elegans* compared with the Control. GO: Gene Ontology (database).

| GO | Name |
|---|---|
| GO: 0016477 | Cell migration |
| GO: 0008406 | Gonad development |
| GO: 0040027 | Negative regulation of vulva development |
| GO: 0042127 | Regulation of cell proliferation |
| GO: 0040020 | Regulation of meiosis |
| GO: 0006511 | Ubiquitin-dependent protein catabolic process |
| GO: 0045167 | Asymmetric protein localization during cell fate |
| GO: 0000070 | Mitotic sister chromatid segregation |
| GO: 0051729 | Germinline cell cycle |
| GO: 0007052 | Mitotic spindle organization |
| GO: 0007098 | Centrosome cycle |
| GO: 0070918 | Production of small RNA involved in gene silencing |
| GO: 0045144 | Meiotic sister chromatid segregation |
| GO: 0032465 | Regulation of cytokinesis |
| GO: 0000079 | Regulation of cyclin-dependent protein serine/threonine kinase activity |
| GO: 0009410 | Response to xenobiotics |
| GO: 0030261 | Chromosome condensation |
| GO: 0007606 | Sensory perception of chemical stimulus |
| GO: 0035046 | Pronuclear migration |
| GO: 0090387 | Phagolysosome assembly involved in apoptotic cell clearance |
| GO: 0045787 | Positive regulation of cell cycle progression |
| GO: 0006261 | DNA replication |
| GO: 0006898 | Receptor-mediated endocytosis |
| GO: 0001714 | Cell fate |
| GO: 0032320 | Positive regulation of GTPase activity |
| GO: 0000281 | Cytokinesis after mitosis |
| GO: 0090068 | Positive regulation of cell cycle process |
| GO: 0030703 | Eggshell formation |
| GO: 0018991 | Oviposition |
| GO: 0006997 | Nucleus organization |
| GO: 0000132 | Mitotic spindle orientation |
| GO: 0040022 | Germline |
| GO: 0006030 | Chitin metabolism |
| GO: 0032506 | Cytokinesis |
| GO: 0032880 | Regulation of protein localization |
| GO: 0040015 | Negative regulation of multicellular organism growth |
| GO: 0045944 | Positive regulation of transcription |
| GO: 0008630 | DNA damage response |
| GO: 0000122 | Negative regulation of transcription |
| GO: 0043066 | Negative regulation of apoptosis |
| GO: 0010638 | Positive regulation of organelle organization |
| GO: 0000398 | Intron elimination/mRNA splicing via spliceosome |
| GO: 0042464 | Dosage compensation by hypoactivation of X chromosome |
| GO: 0007127 | Meiosis |
| GO: 0042693 | muscle cells fate commitment |

TABLE 7-continued

List of the 76 biological processes under-expressed in BIF-1-treated
*C. elegans* compared with the Control. GO: Gene Ontology (database).

| GO | Name |
|---|---|
| GO: 0032012 | Regulation of ARF protein signal transduction |
| GO: 0006310 | DNA recombination |
| GO: 0038032 | G-protein coupled receptor signalling pathway |
| GO: 0016331 | Morphogenesis of embryonic epithelium |
| GO: 0007219 | Notch signalling pathway |
| GO: 0008356 | Asymmetric cell division |
| GO: 0042026 | Protein refolding |
| GO: 0007040 | Lysosome organization |
| GO: 0045595 | Regulation of cell differentiation |
| GO: 0032446 | Protein modification by small protein conjugation |
| GO: 0034968 | Histone methylation |
| GO: 0008595 | Specification of the anterior/posterior axis in embryo |
| GO: 0001703 | Gastrulation with mouth forming |
| GO: 0042176 | Regulation of protein catabolism |
| GO: 0006606 | Protein import into the neuclues |
| GO: 0031114 | Regulation of microtubule depolymerization |
| GO: 0007411 | Axon guidance |
| GO: 0006200 | ATP catabolism |
| GO: 0016055 | Wnt receptor signalling pathway |
| GO: 0000212 | Mitotic spindle organization |
| GO: 0006911 | Phagocytosis |
| GO: 0046777 | Protein autophosphorylation |
| GO: 0035194 | Post-transcriptional gene silencing by RNA |
| GO: 0032269 | Negative regulation of cellular protein metabolism |
| GO: 0006289 | Nucleotide excision repair |
| GO: 0006661 | Phosphatidyl inositol biosynthesis |
| GO: 0048557 | Embryonic gut morphogenesis |
| GO: 0051295 | Establishment of meiotic spindle localization |
| GO: 0006906 | Vesicle fusion |
| GO: 0030071 | Regulation of mitotic metaphase/anaphase transition |
| GO: 0051053 | Negative regulation of DNA metabolism |

In summary, the results of the transcriptomic study show that in the nematodes fed on strain BIF-1 there was an upregulation of the metabolic pathways and processes related to carbohydrate metabolism (oxidative phosphorylation, ATP synthesis, etc.) glutathione metabolism (decreased levels of oxidative stress), biosynthesis of cofactors and vitamins, lipid metabolism, nucleotide metabolism, glycosylation and membrane metabolism.

Example 7

Metabolomic Study in *C. elegans* on Strain BIF-1

We analyzed the changes in the metabolic profile of *C. elegans* after ingestion of strain BIF-1 compared with the profile of Control nematodes (fed NG medium+*E. coli* OP50).

The trials involved feeding *C. elegans* with strain BIF-1 from the egg to the young adult stage (3-day-old). The control feeding condition was NG medium seeded with the bacteria *Escherichia coli*.

After this time, nematodes were subjected to a metabolomic analysis, applying analytical techniques, LC-MS/MS (ESI+) (−ESI) and GC-MS, and subsequent bioinformatic processing of the data.

The results showed statistically significant changes, as listed below:

Glutathione (GSH) metabolism and oxidative stress: In the study, the levels of γ-glutamyl-leucine and γ-glutamyl-methionine were higher in Nematodes fed BIF-1 compared with the Control, which would be consistent with a possible increase the γ-glutamyl-transferase (GGT) activity and thus, recycling of glutathione (GSH) in response to BIF-1. Furthermore, ophthalmate, a metabolite used for GSH synthesis, decreased significantly in the group fed BIF-1, which is consistent with a decrease in GSH biosynthesis. This is probably due to a lower demand for glutathione produced by a lower level of oxidative stress. This is supported by the observation of lower levels of GSSG (oxidized GSH) and cysteine-glutathione disulfide, biomarkers of oxidative stress in the group fed the BIF-1 strain.

Carbohydrate metabolism: The group fed BIF-1 displayed changes in many of the metabolites involved in carbohydrate metabolism. Levels maltotetraose and maltopentaose exhibited high levels, whereas trehalose-6-phosphate and glucose levels were lower in the group fed BIF-1 compared to the Control. Other pathways affected were glycogen metabolism and the pentose phosphate pathway. Thus, 6-phosphogluconate showed a significant increase in the BIF-1 group. This fact together with the high levels of ribose and low levels of ribulosa-5-phosphate are consistent with a possible upregulation of the pentose phosphate pathway in the presence of BIF-1.

Nucleotide Metabolism: Changes in nucleotide metabolism are a consequence of the changes observed in the activity of the pentose phosphate pathway. Nematodes fed BIF-1 showed higher levels of N-carbamoyl-aspartate and orotate, two intermediaries in pyrimidine synthesis. Similar changes were seen in purine metabolism. Thus, BIF-1-treated nematodes showed lower levels of allantoin (product of purine degradation). In addition, the group treated with BIF-1 had higher levels of purine nucleosides (adenosine and guanosine) bases (adenine and hypoxanthine) and nucleotides [adenosine 5'-monophosphate (AMP) and guanosine 5'-monofosfate (GMP)]. These results together with the observed increase in precursor amino acids (glutamate and glutamine), and the possible upregulation of the pentose phosphate pathway, supports a possible increase in purine biosynthesis, accompanied by a decrease in purine degradation.

Metabolism of membrane and cholesterol: In nematodes fed BIF-1, we observed increased levels of choline and acetylcholine, which are involved not only in glycosylation processes, but also in membrane metabolism. Moreover, levels of 7-dihydrocholesterol, an intermediary in cholesterol biosynthesis, were increased in nematodes fed BIF-1, which is consistent with the effect of this probiotics on the modulation of cholesterol biosynthesis. Changes in cholesterol content in the membrane may affect the receptor environment, ion channels and other membrane proteins, and thereby alter their function. Furthermore, cholesterol metabolism affects lipid and hormone-related processes.

Additional observations: In *C. elegans* BIF-1 increased levels of phosphopantetheine, 3'-dephospho-coenzyme-a, and coenzyme A (CoA). Moreover BIF-1 led to an increase in flavin mononucleotide (FMN) and flavin adenine dinucleotide (FAD), consistent with the upregulation of FAD biosynthesis. CoA and FAD are involved in the metabolism of carbohydrates, lipids and amino acids.

In summary, feeding strain BIF-1 to *C. elegans* produces a series of metabolic changes related to the antioxidant metabolism, carbohydrate and nucleotide metabolism. Glutathione metabolism appears to be a target of the probiotic BIF-1 to reduce oxidative stress levels. Furthermore, the BIF-1 diet led to an upregulation of the pentose phosphate and glycosylation pathways. Additionally alterations were observed in the metabolism of glycogen, nucleotides, lipids and cofactors.

These results are consistent with those observed in the transcriptomic study (Example 6).

Example 8

Identification of Differentially Expressed Genes

In order to explain the mechanism of action from the transcriptomics results described in Example 6, we undertook a trial to evaluate body-fat reduction in C. elegans fed strain BIF-1. In this experiment, we employed C. elegans wild-type N2 and different C. elegans mutants in the key genes highlighted by the transcriptomic study. A gene is essential to the mechanism of action of a certain ingredient when the functional effect observed in the C. elegans wild-type N2 wholly or partly disappears in the mutant of that gene. The results shown in Table 8 (attached), and FIG. 6 identify some of the target genes mutated in C. elegans, which are differentially expressed after ingestion of BIF-1 (transcriptomic study). These results explain the biological activities affected by ingestion of the strain of the present invention.

TABLE 8

List of target mutated genes in C. elegans.
TRIALS WITH BIF 1 (B. animalis subsp lactis CECT 8145)

| Biological processes | C. elegans (name of mutated gene appears in brackets) | OBESITY % reduction compared to Control |
|---|---|---|
|  | Wild-type N2 | 29.21 |
| B-oxidation fatty acids in peroxisome | VC1785(Acox-1) | −15.36 |
|  | RB2015(Acs-5) | 12.59 |
|  | RB859(Daf-22) | 19.03 |
| Fatty acid desaturation | BX153(Fat-7) | 0.56 |
|  | GR1307(Daf-16) | −2.63 |
| REDOX homeostasis mechanisms | VC175(Sod-4) | 3.63 |
|  | RB1764(Trxr-2) | −3.3 |
| Oxidative phosphorylation | RB2434(Asg-2) | 5.39 |
| Tryptophan metabolism | GR1321(Tph-1) | 18.19 |

Figure 6:
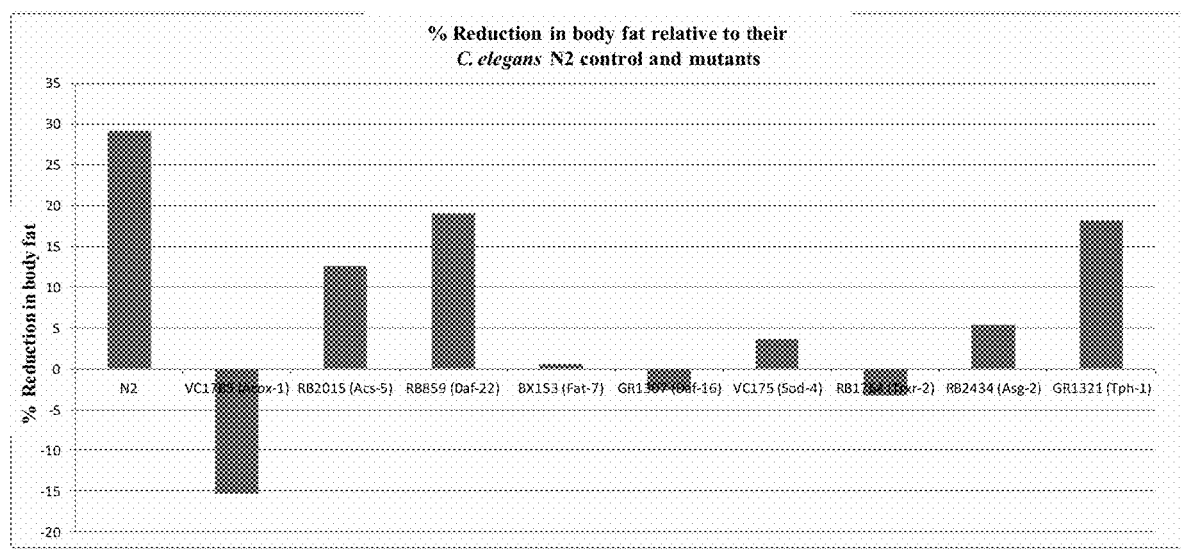
FIG. 6: Reduction in body fat relative to *C. elegans* (wild type N2) and mutants.
Figure 7:
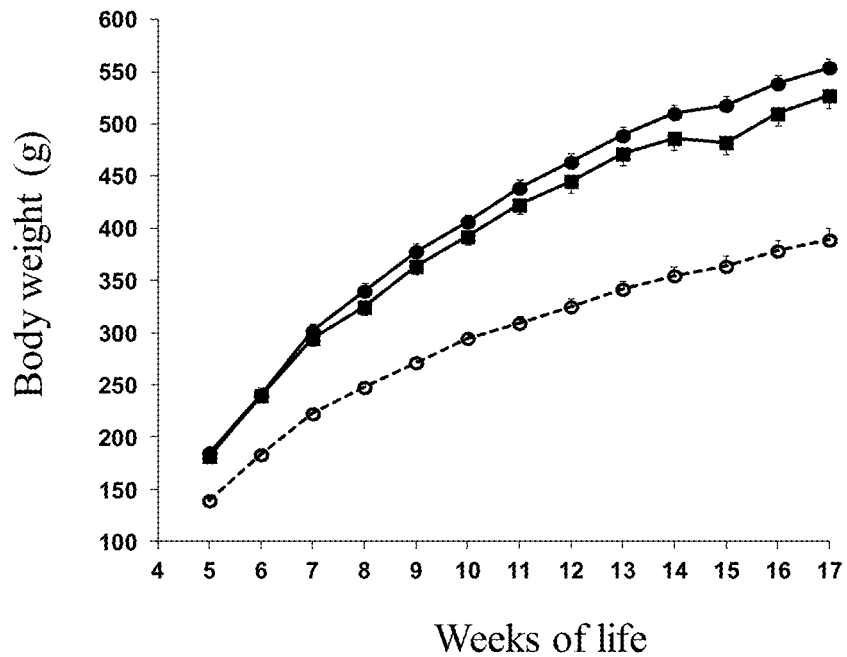
FIG. 7: Determination of body weight in obese Zucker rats treated with $10^{10}$ CFU/day (■) of the strain CECT8145 (BIF-1) during the 17-week trial. A control group of obese Zücker rats (●) and a group of lean Zücker rats (○) were included in the trial.
Figure 8:
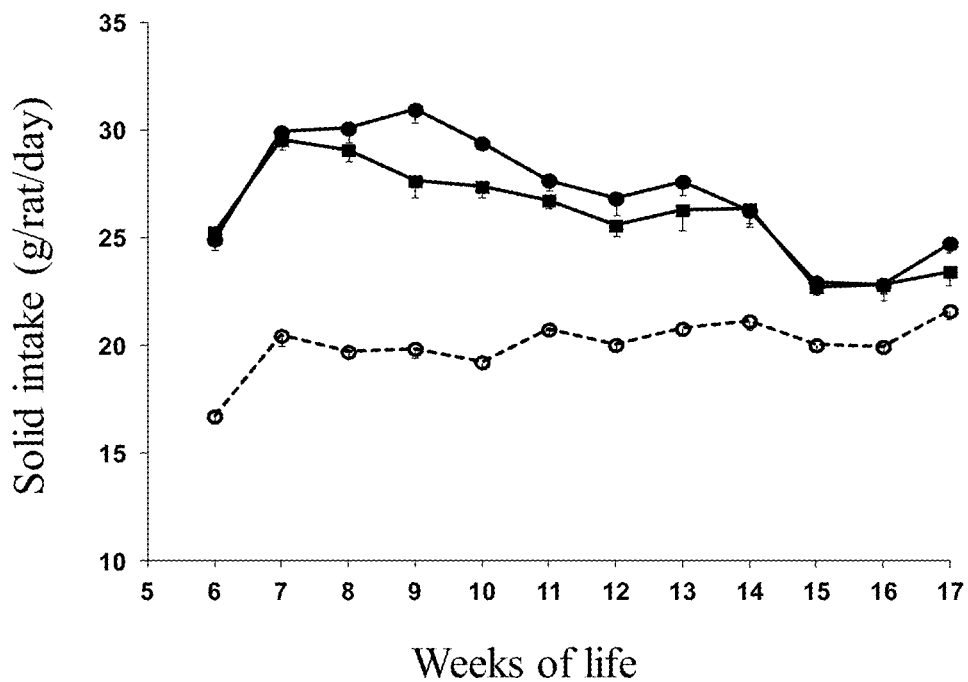
FIG. 8: Solid intake observed in obese Zucker rats treated with $10^{10}$ CFU/day (■) of strain CECT8145 (BIF-1). A control group of obese Zücker rates (●) and a group of lean Zücker rats (○) were included in the trial.
Figure 9:
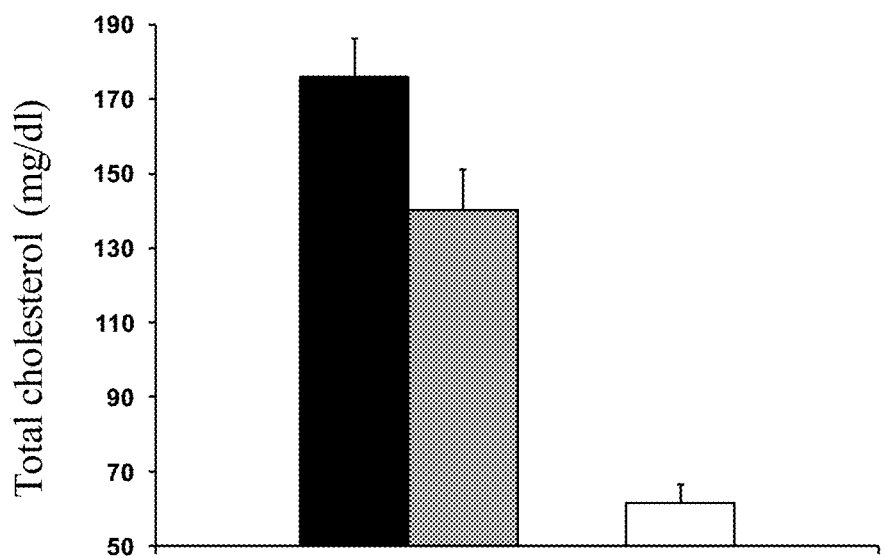
FIG. 9: Total cholesterol in obese Zucker rats treated with $10^{10}$ CFU/day of strain CECT (BIF-1) (gray bar), compared with control Zücker rats (black bar). A control group of lean Zücker rats (white bar) was included in the trial.
Figure 10:
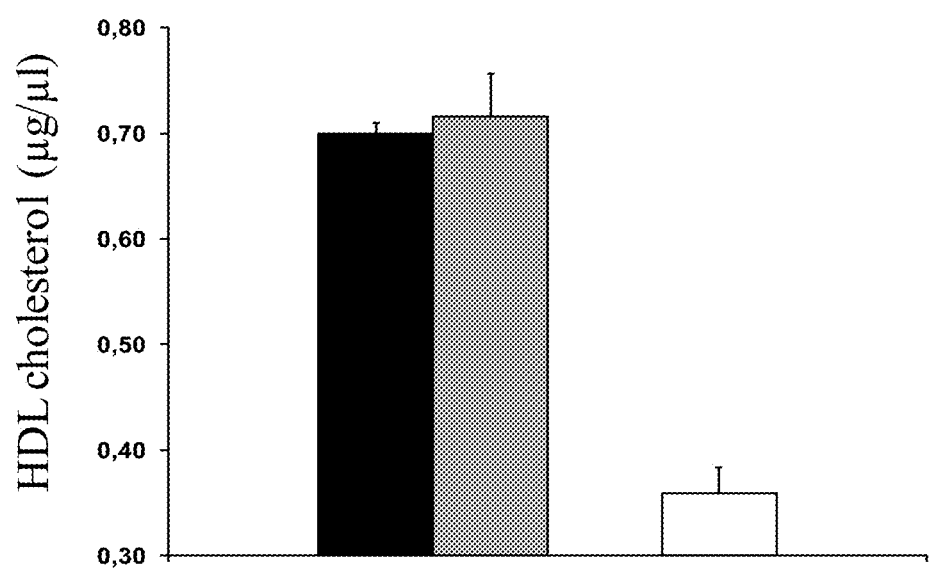
FIG. 10: HDL cholesterol in obese Zucker rats treated with $10^{10}$ CFU/day of strain CECT8145 (BIF-1) (gray bar), compared with control Zücker rats (black bar). A control group of lean Zücker rats (white bar) was included in the trial.
Figure 11:
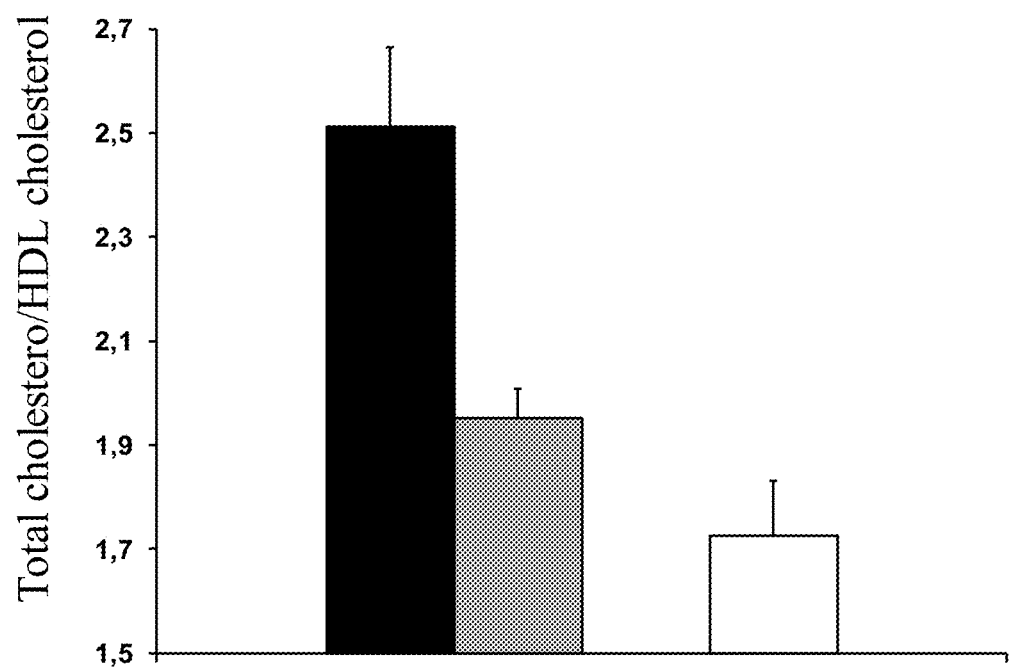
FIG. 11: Ratio total cholesterol:HDL cholesterol (Cardiovascular Risk Index) determined in obese Zucker rats treated with $10^{10}$ CFU/day of strain CECT8145 (BIF-1) (gray bar), compared with control Zücker rats (black bar). A control group of lean Zücker rats (white bar) was included in the trial.
Figure 12:
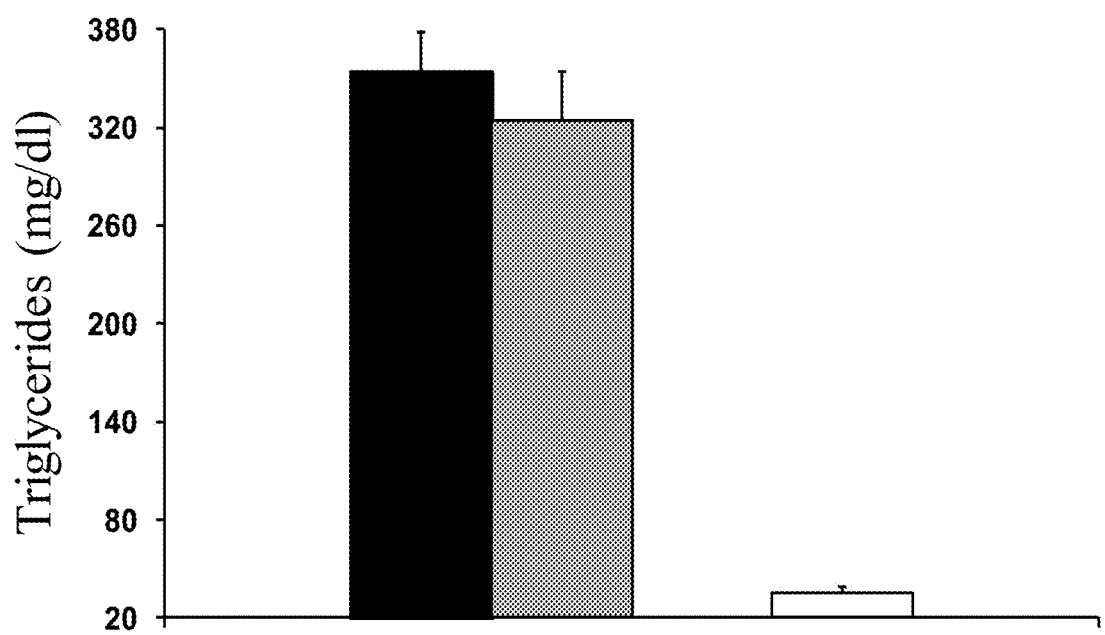
FIG. 12: Triglyceride concentration determined in obese Zucker rats treated with $10^{10}$ CFU/day of strain CECT8145 (BIF-1) (gray bar), compared with control Zücker rats (black bar). A control group of lean Zücker rats (white bar) was included in the trial.
Figure 13:
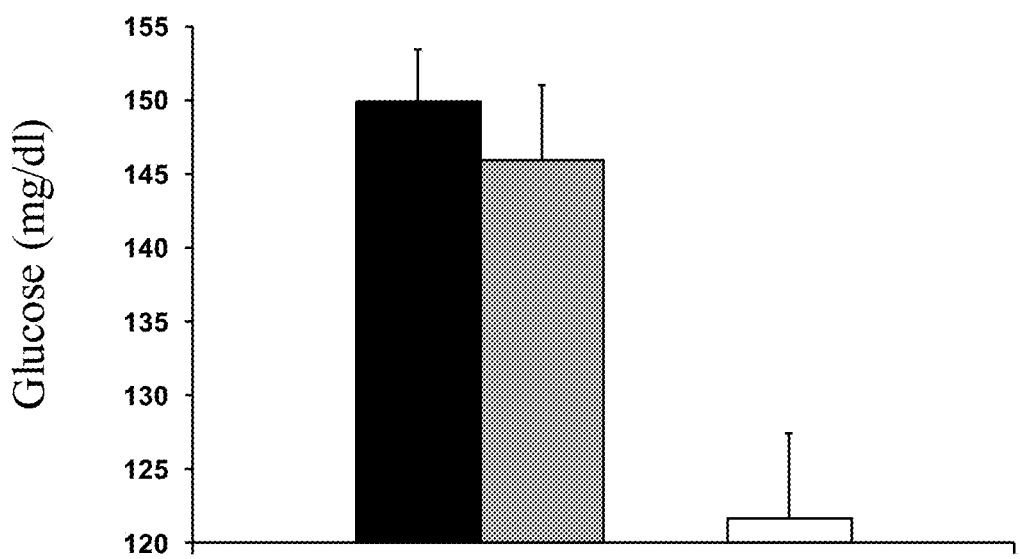
FIG. 13: Glucose concentration determined in obese Zucker rats treated with $10^{10}$ CFU/day of strain CECT8145 (BIF-1) (gray bar), compared with control Zücker rats (black bar). A control group of lean Zücker rats (white bar) was included in the trial.
Figure 14:
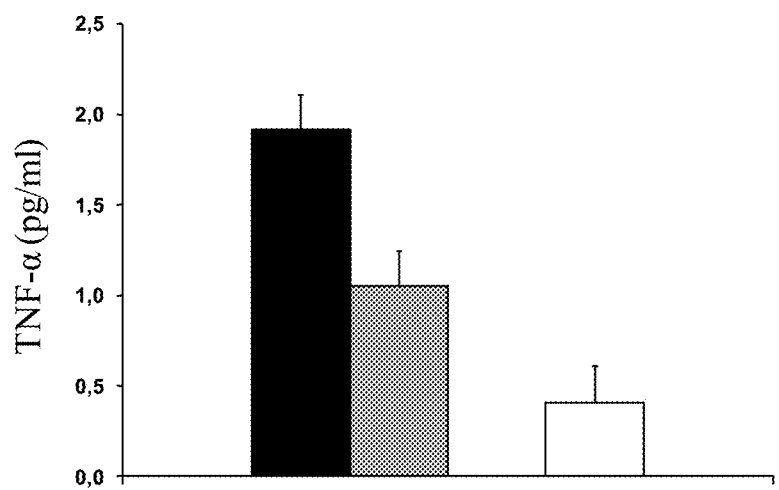
FIG. 14: Levels of TNFα (marker of inflammation) in obese Zücker rats treated with $10^{10}$ CFU/day of strain CECT8145 (BIF-1) (gray bar), compared with control Zücker rats (black bar). A control group of lean Zücker rats (white bar) was included in the trial.
Figure 15:
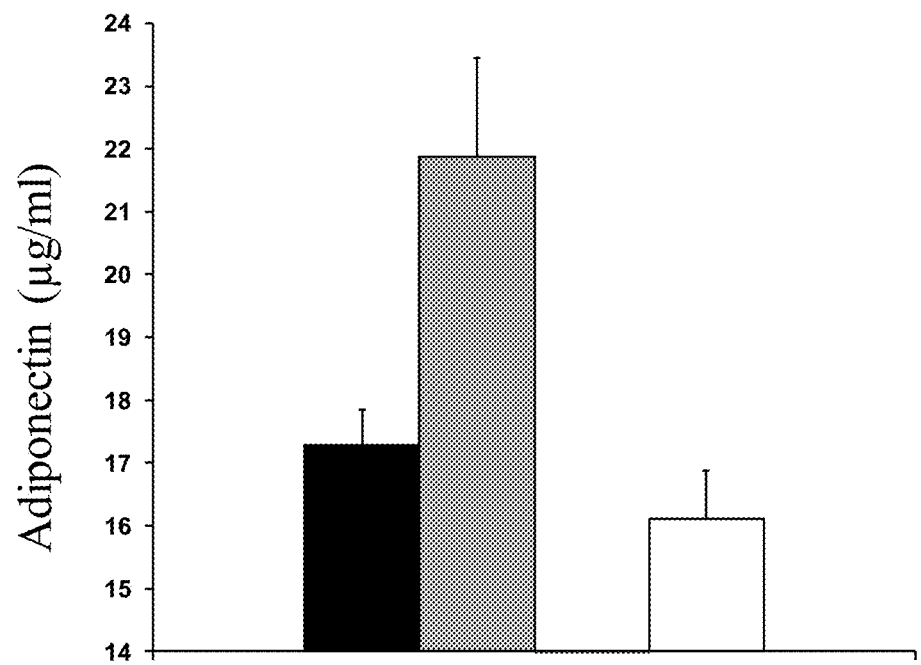
FIG. 15: Adiponectin levels in obese Zucker rats treated with $10^{10}$ CFU/day of strain CECT8145 (BIF-1) (gray bar), compared with control Zücker rats (black bar). A control group of lean Zücker rats (white bar) was included in the trial.
Figure 16:
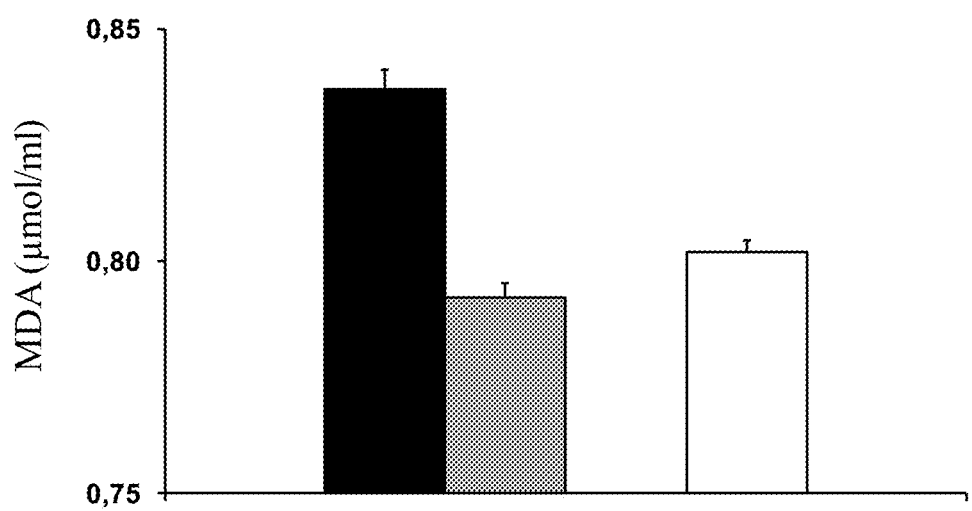
FIG. 16: Concentration of malondialdehyde (marker of oxidation) determined in obese Zucker rats treated with $10^{10}$ CFU/day of strain CECT8145 (BIF-1) (gray bar), compared to control Zücker rats (black bar). A control group of lean Zücker rats (white bar) was included in the trial.
Figure 17:
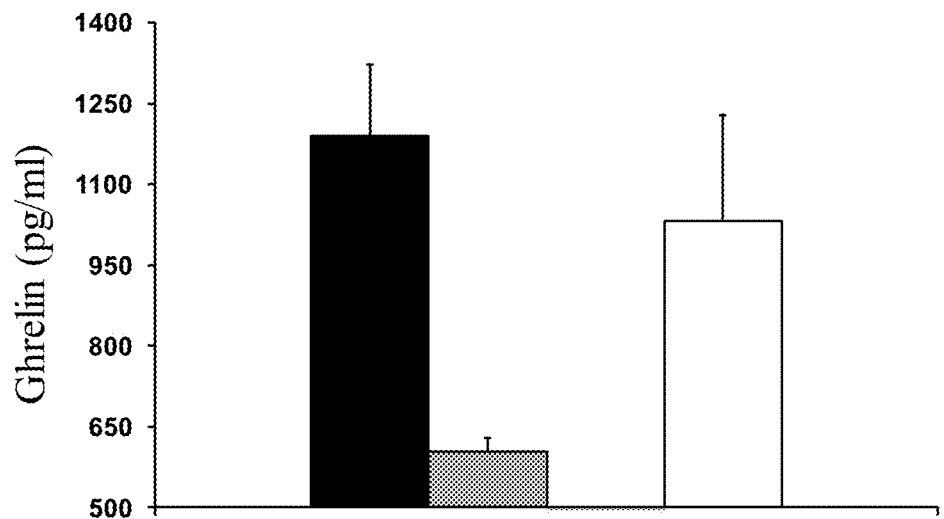
FIG. 17: Ghrelin levels (marker of appetite) determined in obese Zucker rats treated with $10^{10}$ CFU/day of strain CECT8145 (BIF-1) (gray bar), compared to control Zücker rats (black bar). A control group of lean Zücker rats (white bar) was included in the trial.

FIG. 6 quantitatively illustrates the percentage of body-fat reduction in C. elegans wild-type N2 and mutant strains with differential expression of the genes listed in Table 8.

Example 9

Pre-Clinical Trial in a Murine Model

A trial was undertaken in an obese Zucker rat model fed three different doses of the probiotic strain BIF-1 ($10^8$, $10^9$ and $10^{10}$ CFU/day), and included two groups of lean Zucker rats as Control. The trial lasted 12 weeks, body weight was determined, and the solid and liquid intake during the test period was recorded. In addition, at the end of the trial biochemical data were determined: total cholesterol, HDL cholesterol, triglycerides, TNFα factor (inflammation marker), malondialdehyde (marker of oxidative stress), adiponectin and ghrelin (markers of satiety).

The results are shown in FIGS. 7 to 17.

In summary, the results of pre-clinical study in the murine model showed a positive effect on weight reduction in obese Zucker rats fed BIF-1 at doses of $10^{10}$ CFU/day (reduction in weight gain of 6.42% for treatment vs. control group). In addition, animals fed BIF-1 had a lower solid intake. Moreover, the determination of biochemical parameters showed a decrease in total cholesterol, accompanied with an increase in HDL cholesterol in rats fed BIF-1, as well as a slight drop in triglycerides and glucose levels. Finally, BIF-1 treatment resulted in a reduction in levels of TNFα factor, malondialdehyde and ghrelin, while there was an increase of adiponectin.

Example 10

Safety Study

The safety of strain BIF-1 was performed following FAO/WHO guidelines (FAO/WHO, 2002). Specifically, the production of unwanted metabolites was evaluated: lactic acid isomer production (Table 9), bile-salt deconjugation (Table 10) and biogenic amine production (Table 11), and the antibiotic resistance profile (Table 12).

TABLE 9

Production of lactic acid isomers by strain BIF-1

| STRAIN | Lactic acid (g/L of supernatant) | |
|---|---|---|
|  | D-Lactic | L-Lactic |
| BIF-1 | 0.020 ± 0.000 | 2.158 ± 0.025 |

TABLE 10

Bile-salt hydrolysis activity by strain BIF-1 (ND: not detected).

| STRAIN | BSH activity (U.I./mg of protein in cell extract) | | BSH activity (U.I./ml of supernatant) | |
|---|---|---|---|---|
|  | Sodium glycocholate | Sodium taurocholate | Sodium glycocholate | Sodium taurocholate |
| BIF-1 | 0.597 ± 0.028 | 0.127 ± 0.004 | ND | 0.0 ± 0.0 |

TABLE 11

Biogenic amine production by strain BIF-1 (ND: not detected).

| STRAIN | Biogenic amines (μg/ml of supernatant) | | | |
|---|---|---|---|---|
|  | Putrescine | Cadaverine | Histamine | Tyramine |
| BIF-1 | ND | ND | ND | 0.38 ± 0.14 |

TABLE 12

Minimum inhibitory concentration of antibiotics obtained for strain BIF-1.

| Antibiotic | CMI (μg/mL) |
|---|---|
| Gentamicin | 64 |
| Streptomycin | 128 |
| Erythromycin | 0.5 |
| Vancomycin | 1 |
| Ampicillin | 2 |
| Tetracycline | 8 |
| Kanamycin | 128 |
| Chloramphenicol | 4 |
| Clindamycin | 0.25 |

Example 11

Probiotic Properties of Strain BIF-1

Figure 18:
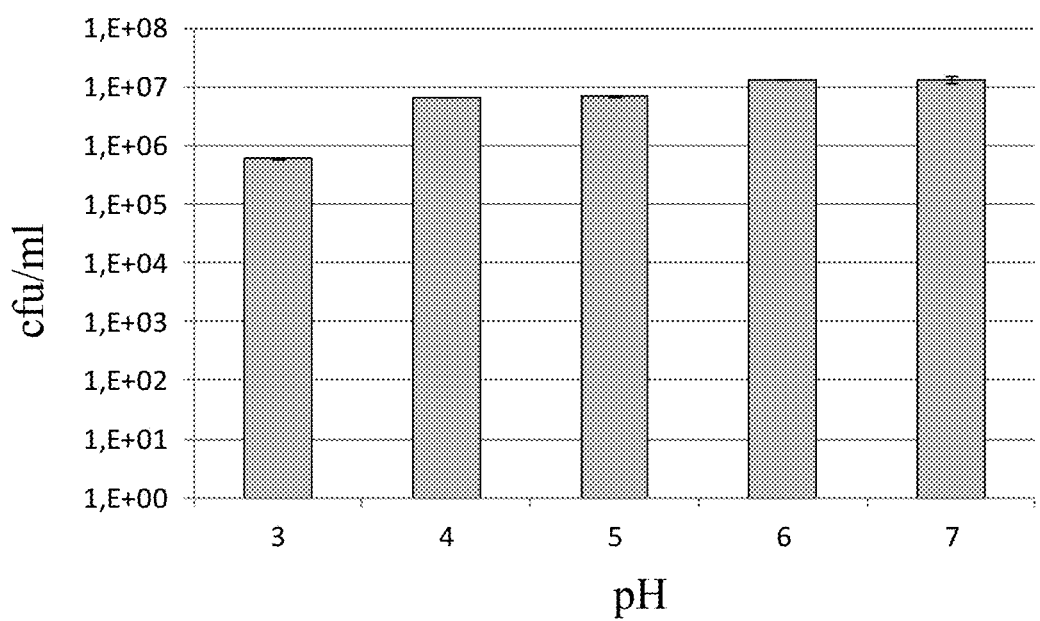
FIG. 18: Resistance of strain BIF-1 to acidic pH levels.
Figure 19:
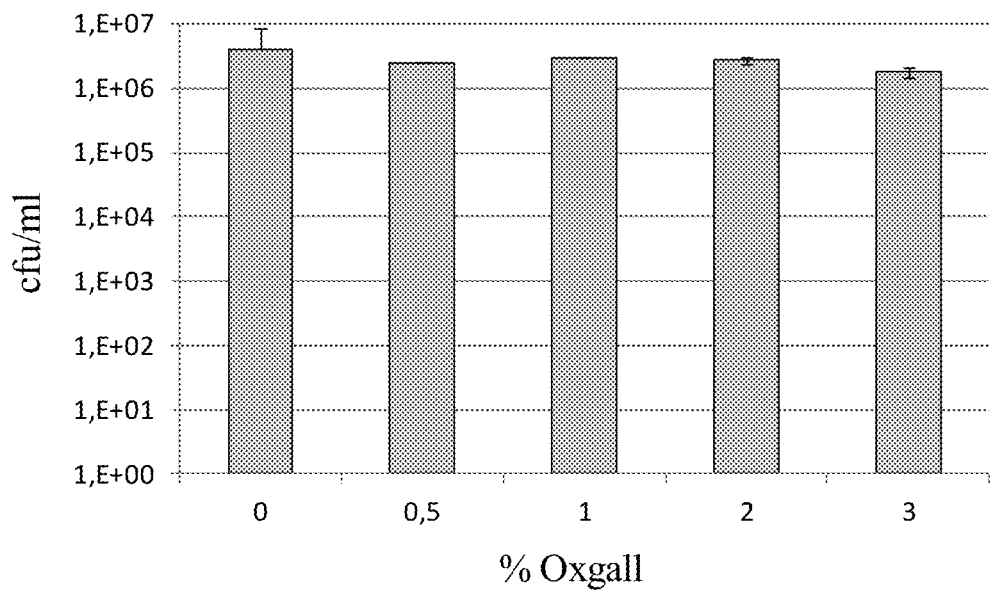
FIG. 19: Resistance of strain BIF-1 to bile salts.

One of the main requirements for a strain to be considered probiotic is that it can survive gastrointestinal transit. Therefore, strain BIF-1 was tested for its resistance to digestive conditions. Accordingly, two tests were performed: one of resistance of low pH levels and the other of resistance to bile salts. In the first, the strain was put into contact with saline solution (0.09% NaCl) at decreasing pH levels for 15 minutes and the number of live cells (FIG. 18) was counted. In the second, strain BIF-1 was put into contact with saline solution with bile salts (Oxgall) in increasing amounts (FIG. 19) for 15 min. Results of these tests did not reveal significant differences in survival rates, except for incubation at pH 4, where a slight loss of viability was detected.

Example 12

Functional Yogurt Fermented with Strain BIF-1 (*Bifidobacterium animalis* subps. *lactis* CECT 8145)

First, the fermentative capacity of BIF-1 was analyzed in a milk matrix. To do so, a volume of commercial skim milk was inoculated with different doses of bacteria ($10^6$, $10^7$ and $10^8$ CFU/mL) and incubated for 24 h at 37° C. The results showed a positive fermentation of the probiotic inoculated at $10^7$ and $10^8$ CFU/mL.

Subsequently, functional yogurt was made by adding $10^8$ CFU/mL of BIF-1 and a mixture of commercial yogurt Bifidobacteria ferments on commercial skim milk and milk powder (0.6%). A control fermentation containing only commercial yogurt strains (*Lactobacillus delbrueckii* subsp. *bulgaricus* and *Streptococcus thermophilus*) was included in the study. Presence of strain BIF-1 was checked at the end of the fermentation by selective plate counting of *Bifidobacterium*.

Figure 20:
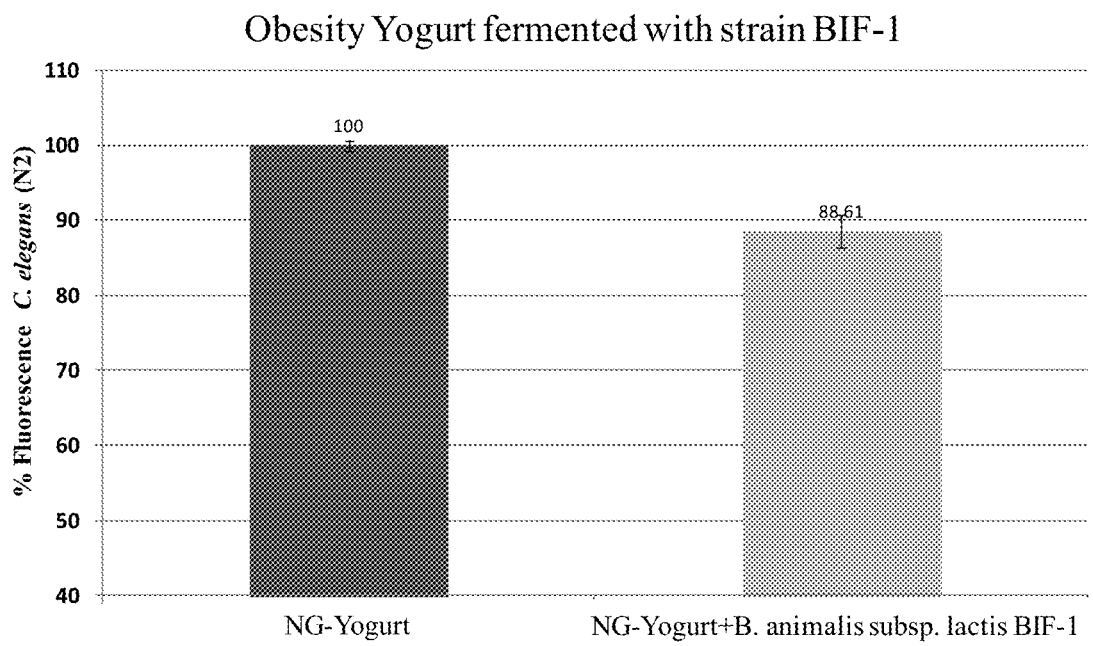
FIG. 20: Yogurt fermented with strain BIF-1 produces greater body-fat reduction in *C. elegans* (11.4%) than conventional commercial yogurt.

Finally, to analyze the effect of the yogurt obtained on reducing body fat, a functional study was performed in the pre-clinical model *C. elegans*. The results show that in *C. elegans*, the yogurt fermented with strain BIF-1 produced a reduction in body fat higher (11.4%) than the conventional commercial yogurt (FIG. 20).

Figure 21:
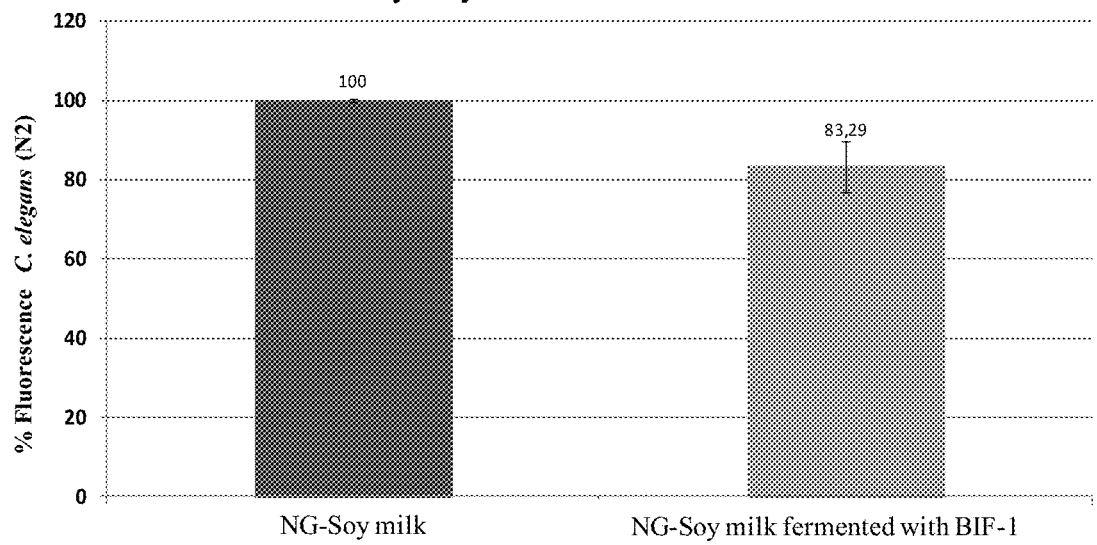
FIG. 21: Fat-reducing effect of soymilk fermented with strain BIF-1 in *C. elegans*.

Also, the same degree of body-fat reduction was determined in *C. elegans* fed soymilk fermented with strain BIF-1 (FIG. 21).

Example 13

Juice Supplemented with Strain BIF-1 (*Bifidobacterium animalis* subps. *lactis* CECT 8145).

Commercial orange juice was supplemented with different doses ($10^6$, $10^7$ and $10^8$ CFU/mL) of active and inactive cells of BIF-1 strain (*Bifidobacterium animalis* subps. *lactis* CECT 8145). In the latter (inactivated cells), the culture was inactivated by autoclave treatment at 121° C. for 30 min. For the functional analysis, the juice supplemented with strain BIF-1 at OD: 30 was added to the surface of the culture medium of *C. elegans* (NG medium). We studied the effect of juice containing thermally inactivated bacteria and live bacteria on body-fat reduction in *C. elegans*.

Figure 22:
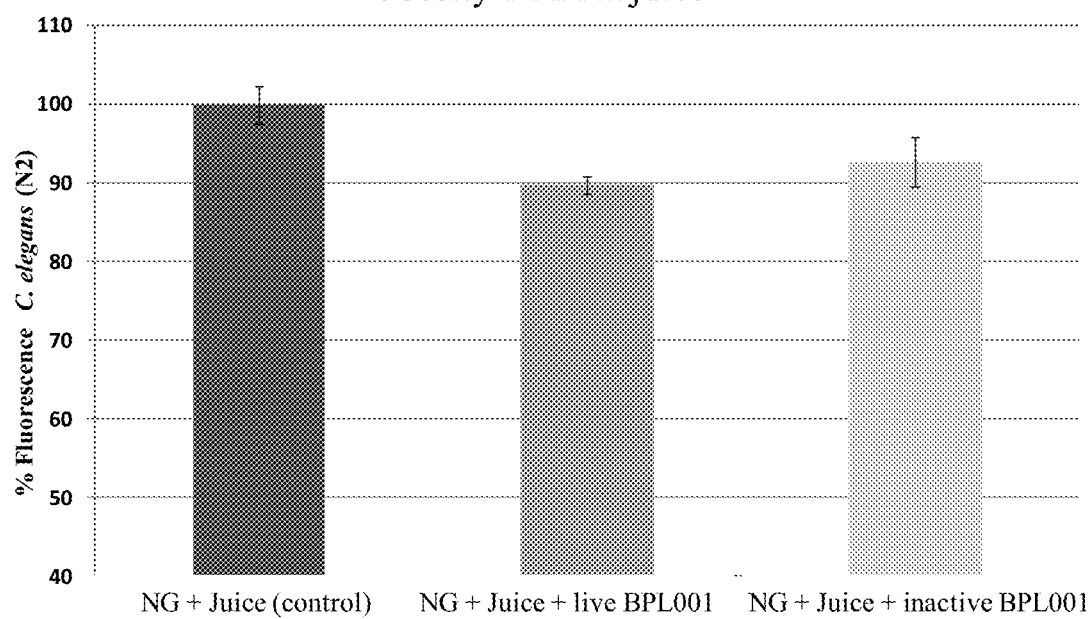
FIG. 22: Fat-reducing effect of juice with strain BIF-1, live and inactivated cells, in *C. elegans*.

The results (FIG. 22) show that nematodes fed the juice supplemented with $10^7$ CFU/mL of live cells of strain BIF-1 experienced a reduction in body fat of 10.3% over control conditions (NG medium). Furthermore, the reduction observed in nematodes fed juice with $10^7$ CFU/mL of inactivated cells of strain BIF-1 was very similar, showing a 7.2% reduction in fat compared to the Control.

The invention claimed is:

1. A composition comprising:
   a strain belonging to the species *Bifidobacterium animalis* subsp. *Lactis* of accession number CECT8145;
   and a food formulation selected from the group consisting of fruit juice, vegetable juice, ice cream, infant formula, milk, yogurt, cheese, fermented milk, powder milk, cereals, bakery products, cereal-based products, nutritional supplements, soft drinks and dietary supplements.

2. The composition according to claim 1, wherein the strain is in the form of viable cells.

3. The composition according to claim 1, wherein the strain is in the form of nonviable cells.

4. The composition according to claim 1, wherein the strain is present in an amount of between $10^5$ CFU and $10^{12}$ CFU per gram or millilitre of the composition.

5. The composition according to claim 1, wherein the composition is a pharmaceutical composition.

6. The composition according to claim 1, comprising at least one other microorganism selected from the group consisting of *Lactobacillus*, *Streptococcus*, *Bifidobacterium*, *Saccharomyces*, *Kluyveromyces*, *L. rhamnosus*, *L. delbrueckii* subsp. *bulgaricus*, *L. kefir*, *L. parakefir*, *L. brevis*, *L. casei*, *L. plantarum*, *L. fermentum*, *L. paracasei*, *L. acidophilus*, *L. paraplantarum*, *L. reuteri*, *S. thermophilus*, *B. longum*, *B. breve*, *B. bifidum*, *B. catenulatum*, *B. adolescentis*, *B. pseudocatenulatum*, *S. cerevisiae*, *S. boulardii*, *K. lactis*, and *K. marxianus*.

7. A method for the treatment of overweight, obesity, or related diseases comprising administering to a subject in need thereof a therapeutically effective amount of the composition according to claim 1.

8. The method according to claim 7, wherein the related diseases are selected from the group consisting of metabolic syndrome, hypertension, glycemia, inflammation, type-2 diabetes, cardiovascular disease, hypercholesterolemia, hormonal disorders and infertility.

* * * * *